(12) United States Patent
Ulrich et al.

(10) Patent No.: US 7,897,786 B2
(45) Date of Patent: Mar. 1, 2011

(54) UNSATURATED DIPYRROMETHENE-BORON BOROCARBONS

(75) Inventors: Gilles Ulrich, Strasbourg (FR); Raymond Ziessel, Souffelweysheim (FR); Christine Goze, Rammersmatt (FR)

(73) Assignees: Centre National de la Recherche Scientifique (C.N.R.S.), Paris (FR); Universite Louis Pasteur de Strasbourg, Strasbourg (FR)

( * ) Notice: Subject to any disclaimer, the term of this patent is extended or adjusted under 35 U.S.C. 154(b) by 589 days.

(21) Appl. No.: 11/884,360

(22) PCT Filed: Feb. 14, 2006

(86) PCT No.: PCT/FR2006/000333

§ 371 (c)(1),
(2), (4) Date: Nov. 21, 2007

(87) PCT Pub. No.: WO2006/087459

PCT Pub. Date: Aug. 24, 2006

(65) Prior Publication Data

US 2008/0102534 A1      May 1, 2008

(30) Foreign Application Priority Data

Feb. 15, 2005   (FR)   .................... 05 01518

(51) Int. Cl.
*C07D 209/56*     (2006.01)
(52) U.S. Cl. .................... 548/405; 548/400
(58) Field of Classification Search ............. 548/400, 548/405; 514/408, 411
See application file for complete search history.

(56) References Cited

FOREIGN PATENT DOCUMENTS

EP    1 253 151 A1    10/2002

OTHER PUBLICATIONS

Ulrich et al., "Pyrromethene Dialkynyl Borane Complexes for "Cascatelle" Energy Transfer and Protein Labeling," Angew. Chem. Int. Ed., vol. 44, pp. 3694-3698 (May 25, 2005).

*Primary Examiner*—Golam M Shameem
(74) *Attorney, Agent, or Firm*—Young & Thompson

(57) ABSTRACT

The invention relates to unsaturated dipyrromethene-boron borocarbons of formula (I) and the use thereof for fluorescence or electroluminescent analysis. The fluorescent properties are provided by the central ring of six atoms comprising the —N—B—N— sequence, $R^1$ to $R^7$ permitting the modification of the compound properties (fluorescence emission wavelength, quantitative fluorescent yield), at least one of the substituents $S^1$ and $S^2$ has a chromophore end group which permits an excitation of the molecule at wavelengths close to those of the substituent chromophore. A preferably selected from the chromophore substituents with a wavelength close to the ultraviolet which significantly increases the Stokes displacement.

29 Claims, 7 Drawing Sheets

UNSATURATED DIPYRROMETHENE-BORON BOROCARBONS

BACKGROUND OF THE INVENTION

1. Field of the Invention

The present invention relates to unsaturated dipyrromethene-boron borocarbons, and to the use thereof for fluorescent or electroluminescent analysis.

2. Description of the Related Art

Fluorescent labels are currently often used for taking qualitative and quantitative measurements in the fields of immunology, molecular biology, medical diagnostics or for DNA chips.

One of the properties required for a chemical compound which can be used as a fluorescent label is an increased Stokes shift, Stokes shift being the energy difference between excitation and emission of the compound. Using labels with a low Stokes shift requires the use of specific filters to eliminate residual excitation light, and this reduces the sensitivity of the measurement.

Examples of the many compounds in the prior art which can be used as fluorescent labels include, in particular, dipyrrometheneboron difluorides (referred to hereinafter as BODIPY). U.S. Pat. No. 4,774,399 describes BODIPY compounds which have dye properties and which contain functional groups capable of forming a stable fluorescent product with functional groups of biological molecules or polymers, said molecules being detected by their absorption and fluorescent properties. U.S. Pat. No. 5,187,288 describes BODIPY compounds which have a maximal absorption peak at wavelengths greater than approximately 525 nm, and are electrically neutral, photostable and, in most cases, highly fluorescent. U.S. Pat. No. 5,248,782 describes BODIPY compounds with dye properties and which comprise heteroaryl substituents. U.S. Pat. No. 5,274,113 describes BODIPY compounds which are fluorescent dyes having a maximal absorption peak at wavelengths greater than approximately 525 nm, and are chemically reactive towards nucleic acids, proteins, carbohydrates, and other biological compounds. U.S. Pat. No. 5,338,854 describes compounds which are fluorescent fatty acid analogues derived from dipyrrometheneboron difluoride and have a maximal absorption peak at wavelengths greater than approximately 480 nm. U.S. Pat. No. 5,451,663 describes compounds which are fluorescent dyes having a maximal absorption peak at wavelengths greater than approximately 525 nm, and are chemically reactive towards nucleic acids, proteins, carbohydrates, and other biological compounds. U.S. Pat. No. 4,916,711 describes a method for generating laser light using BODIPY compounds. U.S. Pat. No. 5,189,029 describes a method for treating cancer tumours using three specific BODIPY compounds. U.S. Pat. No. 5,446,157 refers to a BODIPY compound family. U.S. Pat. No. 5,852,191 describes dipyrrometheneboron dihalides which are blue-fluorescing dyes which are highly fluorescent and light-absorbent and which may be used in various biological and non-biological applications. U.S. Pat. No. 5,446,157 refers to another BODIPY compound family.

The majority of the compounds mentioned hereinbefore have fluorescent properties. However, they all have a relatively low Stokes shift ($\Delta v \approx 500$ to $600$ cm$^{-1}$) which means that, when they are used as labels, their sensitivity is not optimal due to a filter being used.

SUMMARY OF THE INVENTION

The present inventors have found that by replacing at least one of the fluorine atoms on the boron in the dipyrrometheneboron difluoride-type compounds with a suitable substituent, compounds with a substantially higher Stokes shift can be obtained in comparison to equivalent bifluorinated compounds, said compounds consequently having a markedly improved sensitivity when used as labels for fluorescent or electroluminescent analysis.

The object of the present invention is to provide compounds with an improved Stokes shift, a high quantum yield of fluorescence, and very high molar absorption coefficients, in which compounds the excitation wavelength and the emission wavelength can be monitored. Said compounds are particularly suitable for use as fluorescent labels or for electroluminescence.

The compounds according to the present invention correspond to the general formula (I)

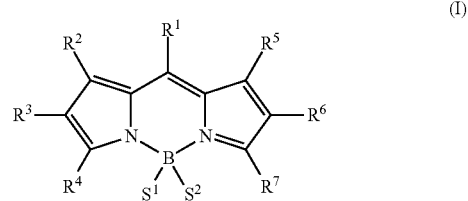

(I)

in which:
each of the substituents $R^1$, $R^2$, $R^3$, $R^4$, $R^5$, $R^6$ and $R^7$ is selected independently of the other substituents from the group consisting of H, -L-H radicals, -G radicals and -L-G radicals,
or the two substituents $R^3$ and $R^4$ together form a divalent radical $Z^{34}$ and/or the two substituents $R^6$ and $R^7$ together form a divalent radical $Z^{67}$, said divalent radicals being such that they form, with the carbon atoms to which they are bound, a structure selected from the group consisting of one ring or two condensed rings, each ring having 5 or 6 atoms and comprising carbon atoms and at most two heteroatoms selected from N, O and S;
L is a binding group consisting of a single bond, or consisting of one or more segments selected from alkylenes and linear or branched alkenylenes optionally comprising in their chain one or more oxygen atoms forming ether radicals, alkynylenes and arylenes comprising a single ring or a plurality of condensed or non-condensed rings;
G is a functional group;
the substituents $S^1$ and $S^2$ each independently represent F; a radical selected from the group defined for the substituents $R^1$ to $R^7$; or a radical corresponding to the formula —C≡C-L'-A, which L' is a single bond or a radical selected from the group defined for L, and A is a chromophoric group or a functional group capable of binding with a biological molecule, an inorganic compound, or a polymeric or non-polymeric organic compound; it being understood that at least one of $S^1$ and $S^2$ is a —C≡C-L'-A radical.

The fluorescent properties are conferred to the molecules of the invention basically by the central cycle of 6 atoms comprising the sequence —N—B—N—.

The selection of substituents $R^1$ to $R^7$ (where necessary, collectively referred to hereinafter as $R^i$) allows the properties of the compound to be modified, for example, the fluorescence emission wavelength, the quantum yield of fluorescence, the solubility and the dipole moment, by selecting binding group L and/or end group H or G.

Binding group L preferably consists of a single bond, or an alkylene segment having from 1 to 10 carbon atoms, in particular 1 to 6 carbon atoms, and/or a phenylene segment, and/or an alkynylene segment having from 2 to 4 carbon atoms, and/or an alkenylene segment having from 2 to 4 carbon atoms, and/or a polyether segment [for example a poly(ethylene oxide) segment] having from 1 to 12 oxygen atoms.

The terminal functional group G is intended to confer the required properties to the compound. It may be selected from:

Polar groups which increase the solubility of the compound in water (for example amide, sulphonate, sulphate, phosphate, quaternary ammonium, hydroxyl, phosphonate, polyoxyethylene groups);

Electron donor groups and electroattractive groups which shift the absorption and emission wavelengths of the fluorescent molecule (for example cyano, nitro, fluoroalkyl, perfluoroalkyl, amide, nitrophenyl, substituted triazino, sulphonamide, alkenyl and alkynyl groups), it being understood that, in this case, the binding group L is selected from alkenylene or alkynylene segments having from 2 to 4 carbon atoms;

The reactive functional groups which allow the compound according to the invention to be grafted onto a biological molecule, forming a labelled compound which allows a compound present in a medium to be detected and quantified (for example, the compound obtained by grafting a compound according to the invention on an antibody allows the corresponding antigen to be detected);

The functional groups capable of reacting with an organic or inorganic compound to be detected in a medium, forming a strong bond (covalent or ionic bond) or weak bond (hydrogen bond) with said compound to be detected.

The substituents $S^1$ and $S^2$ are collectively referred to hereinafter as $S^i$ where necessary.

A substituent $S^i$ in which the end group A is a chromophoric group allows the molecule to be excited in the wavelengths close to the chromophoric substituent A, which is preferably selected from chromophoric substituents having a wavelength close to that of ultraviolet rays, which strongly increases the Stokes shift. This effect is accentuated if the two substituents $S^i$ carry a chromophoric end group.

In one embodiment, at least one of the substituents $S^i$ is a —C≡C-L'-A group, in which L' is a single bond or an alkylene segment having from 1 to 10 carbon atoms or a polyether segment having from 1 to 12 carbon atoms, and A is a chromophoric radical selected from:

aryl radicals having an aromatic ring optionally carrying substituents (for example p-toluoyl, styrenyl, pyridinyl, oligopyridinyls (in particular bipyridinyl and terpyridinyl), thienyl, or pyrrolyl), aryl radicals having at least two condensed rings (such as naphthyl, pyrenyl, anthracenyl, phenanthrenyl, quinolyl, phenanthronyl, perylenyl, fluorenyl, carbazolyl and acridinyl), said radicals optionally carrying at least one substituent (selected, for example, from the group consisting of sulphonato, amino, nitro, hydroxy, ether and halogeno radicals);

radicals with dye properties, such as coumarinyl, hydroxycoumarinyl, alkoxycoumarinyl, trisulphonatopyrenyl, cyanine, styrylpyridinium, naphthalimidinyl or phenylphenanthridium radicals.

If a compound according to the invention is intended to be bound to another compound, at least one of the substituents $S^i$ is a —C≡C-L'-A group or at least one of the substituents $R^i$ is an -L-G group, A or G being a radical which allows the compound according to the invention to bind to said other compound. In a preferred embodiment, L' or L is a single bond or an alkylene having from 1 to 10 carbon atoms or a polyether segment having from 1 to 12 carbon atoms.

If only one $S^i$ radical is of the —C≡C-L'-A type, the second radical $S^i$ is advantageously selected from F, mononuclear aryl radicals optionally carrying a substituent and aryl radicals comprising at least two condensed rings.

If the compound according to the invention is intended to be bound to a polymeric compound, radical A or radical G is preferably selected from H, trialkylsilyls, or a crosslinking group such as a methacrylate, vinyl, styryl, anilino, pyrrolyl, thiophenyl, furyl, isocyanato or epoxide group. The polymer may be, for example, polystyrene, polyacrylate, polymethacrylate, polyamide, polyurethane, polyepoxide, poly(ethylene oxide), poly(vinyl chloride), or a natural polymer such as cellulose, latex or a natural textile fibre.

If a compound according to the invention is intended to be bound to a biological molecule, radical A or radical G is preferably selected from the group consisting of succinimidyl ester, sulphosuccinimidyl ester, isothiocyanate, isocyanate, iodoacetamide, maleimide, halosulphonyls, phosphoramidites, alkylimidates, arylimidates, halogenoacids, substituted hydrazines, substituted hydroxylamines and carbodiimides. The biological molecule may be, for example, a protein, a nucleotide or an antibody.

A functional group A or G capable of interacting with an organic compound or a metal salt, of which the presence and quantity in a medium is to be detected and determined, is a functional group capable of forming a strong bond (covalent or ionic bond) or a weak bond (hydrogen bond) with said compound to be detected. Examples of radicals of this type include amino, ureido, hydroxyl, sulphhydryl, carboxyl, carbonyl or crown ether groups. Crown ether radicals in particular allow the detection of alkaline ions.

A compound according to the invention can be bound to an inorganic compound, specifically for the production of optical or optoelectronic devices (for example, light-emitting diodes or photovoltaic devices). The inorganic compound may be, for example, a silica, an alumina, a zeolite, a metal, silicon or a titanium oxide. In this case, radical A or group G is selected from the functional groups capable of forming strong bonds with inorganic materials. For example, a carboxylate group allows the compound to be grafted onto titanium oxides, zeolites or alumina; thiol or thioether groups allow the compound to be bound to a metal (for example Au or Ag); a siloxane group allows the compound to be bound to silica and to the oxidised surface of silicon.

If a compound according to the invention is intended to be used on account of its fluorescent or luminescent properties, compounds which comprise at least one substituent $S^i$ carrying a chromophoric end group A and at least one substituent $S^i$ carrying a grafting group or at least one substituent $R^i$ carrying a grafting group are most preferably used.

BRIEF DESCRIPTION OF THE DRAWING FIGURES

DETAILED DESCRIPTION OF THE INVENTION

Figure 1:
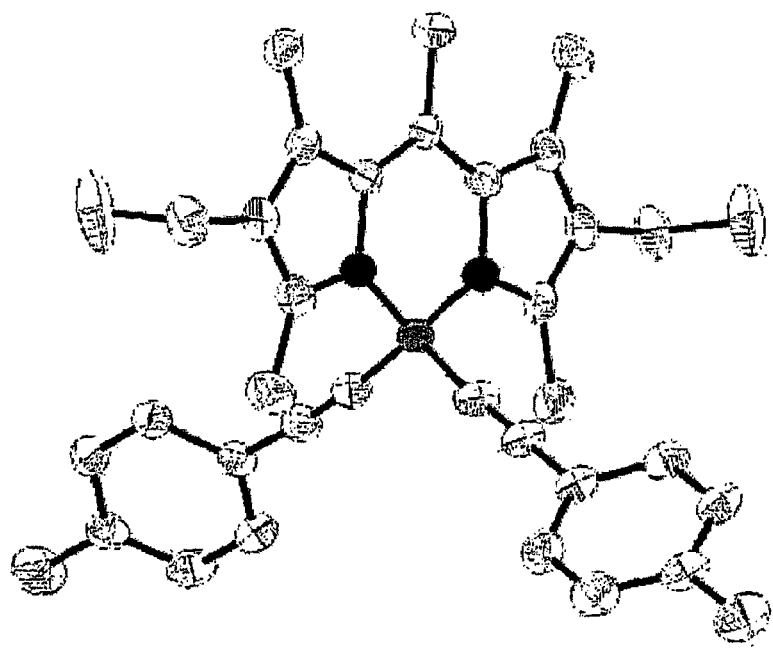
FIG. 1 shows the structure of compound 1, obtained by single-crystal X-ray diffraction.

A particular family of compounds according to the invention comprises the compounds corresponding to formula (I) which are symmetrical, i.e. $R^2$ and $R^5$ are identical, $R^3$ and $R^6$ are identical, $R^4$ and $R^7$ are identical, $S^1$ and $S^2$ are identical. They may be represented by the following formula (II):

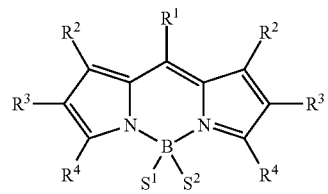

(II)

Another particular compound family corresponds to general formula (I) in which the two substituents of each pentacycle together form a biradical. These compounds may be represented by the following formula (III):

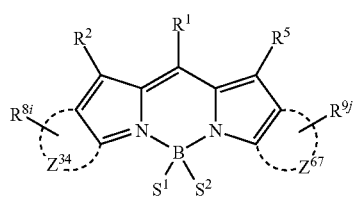

(III)

in which the substituents $R^{8i}$ and $R^{9j}$ are selected independently of one another from the group defined for the substituents $R^1$ to $R^7$.

Compounds of this type may be obtained from many indole groups, which are known to the person skilled in the art in this field and are commercially available.

A compound (I) according to the present invention is generally obtained from corresponding dipyrrometheneboron difluoride which corresponds to formula (I') which is identical to formula (I), $S^1$ and $S^2$ each representing F. If the desired substituents $R^1$ to $R^8$ cannot be obtained directly from dipyrrometheneboron (I'), the compound (I) is modified by suitable reactions, which are known to the person skilled in the art.

An asymmetrical compound (I) is also obtained from corresponding dipyrrometheneboron difluoride (I'). In this case, (I') may be obtained by reacting a ketopyrrole with a pyrrole in the presence of an acid (for example HBr or trifluoroacetic acid (TFA)) according to the following reaction pattern, for which a detailed mode of operation is described specifically in the aforementioned U.S. Pat. No. 4,774,339.

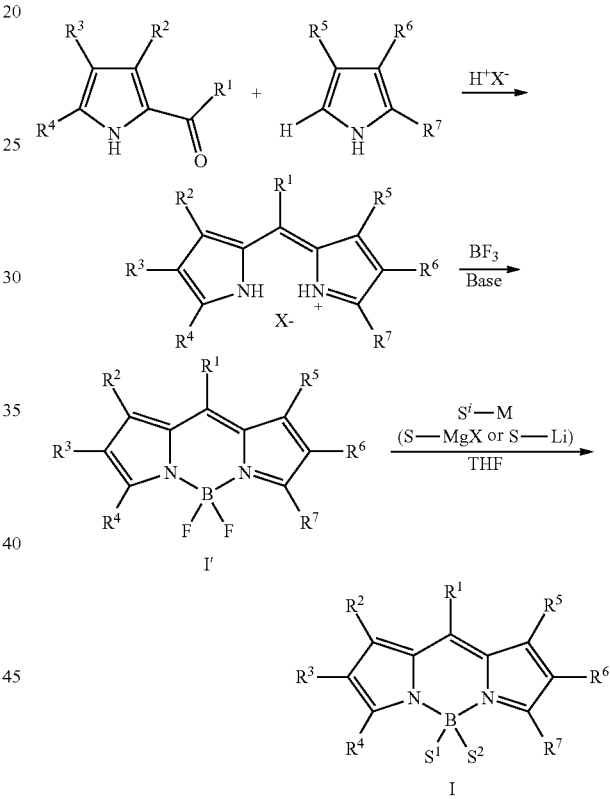

(I') is subsequently subjected to the action of a suitable reagent to replace the atoms F with the desired substituents. The reagent may be selected from organometallic compounds, (for example, an organomagnesium or organolithium compound), in an anhydrous solvent (THF, for example), at a suitable temperature between −20° C. and 40° C. X is a halogen atom. In order to prepare a compound (I) having two identical $S^i$, two equivalents of the organometallic compound of S, $S^i$-MX, are used. In order to prepare a compound (I) with two different $S^i$, a 1/1 mixture of the two organometallic compounds $S^1$-MX and $S^2$-MX is used, and the desired product is separated by chromatography.

A symmetrical compound (II) may be obtained from the corresponding dipyrrometheneboron difluoride (II'), itself obtained from the appropriate pyrrole according to the following reaction pattern:

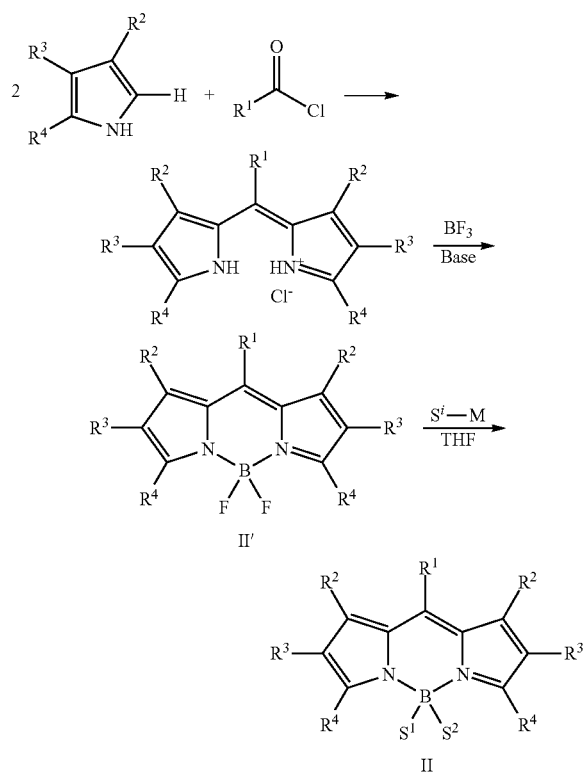

A similar method is described in U.S. Pat. No. 5,189,029 and in U.S. Pat. No. 5,446,157. It consists in reacting pyrrole with $R^1COCl$ in a suitable solvent (for example, dichloroethane or toluene), subsequently reacting the pyrromethene hydrochloride obtained in the same solvent with a trifluoroboron etherate in the presence of a base in order to obtain the dipyrromethene boron difluoride (II'). (II') is subsequently subjected to the action of a suitable reagent to replace the atoms F with the desired substituents. The reagent is of the same type as that used in the corresponding step in the method for preparing symmetrical compounds (I), and the reaction conditions are similar.

Depending on whether it is symmetrical or asymmetrical, a compound (III) is obtained from the pyrrole or from the two appropriate pyrroles, in which the substituents $R^3$ and $R^4$ on the one hand, and $R^6$ and $R^7$ on the other, together form appropriate biradicals $Z^{34}$ and $Z^{67}$ respectively. The atoms F are subsequently replaced by the methods similar to those which produce type (II) compounds.

The $R^i$ substituents on the pyrroles which are commercially available and which may be used as starting products are very varied. Examples of substituent types include alkyl, phenyl or ester. They may be modified to obtain the desired substituents $R^i$. For example:

the ester end groups may be hydrolysed to yield the corresponding acid, which may subsequently be activated in the form of succinimide, for example in preparation for being grafted on a protein;

a nitrophenyl group may be reduced (for example by hydrogen in the presence of a suitable catalyst) to yield the corresponding aromatic amine, which is subsequently activated with thiophosgene to obtain an isothiocyanate, a radical of this type allowing compounds carrying an OH group to be grafted;

active end groups which have been previously protected by known methods, may be unprotected. For example, an amine protected by a Boc on the pyrrole will be unprotected on the desired compound (I).

The present invention is illustrated in the following examples, but is not limited thereto.

In examples 1 to 20, the prepared compounds correspond to general formula (I), $R^1$, $R^2$, $R^4$, $R^5$ and $R^7$ each representing a methyl, $R^3$ and $R^6$ each representing an ethyl (Examples 1 to 17 and 20) or a hydrogen (Examples 18 and 19). The difluorinated compounds used are compounds which correspond to one of the formulae I' or II' and which are described in the literature. The specific selections of the substituents $S^1$, $S^2$ and $R^1$ for the 19 compounds prepared are listed in the following Table 1. Said compounds are analogues, in terms of the fluorescence emission wavelength, of Rhodamine 6G (compounds in Examples 1 to 17 and 20) and Fluorescein (compounds in Examples 18 and 19) respectively.

TABLE 1

| No. | $S^1$ | $S^2$ | $R^1$ |
|---|---|---|---|
| 1 | toluyl-1-ethynyl | p-CH$_3$C$_6$H$_4$—C≡C— | CH$_3$— |
| 2 | Me$_3$Si—C≡C— trimethylsilyl-1-ethynyl | Me$_3$Si—C≡C— | CH$_3$— |
| 3 | H—C≡C— ethynyl | H—C≡C— | CH$_3$— |
| 4 | pyrenyl-1-ethynyl | pyrenyl-1-ethynyl | CH$_3$— |
| 5 | pyrenyl-1-ethynyl | pyrenyl-1-ethynyl | pyrenyl- |

TABLE 1-continued

| No. | S¹ | S² | R¹ |
|---|---|---|---|
| 6 | pyrenyl-1-ethynyl | pyrenyl-1-ethynyl | ethynyl-phenyl iodo-phenyl |
| 7 | pyrenyl-1-ethynyl | pyrenyl-1-ethynyl | ethynyl-phenyl-pentanoic acid |
| 8 | pyrenyl-1-ethynyl | pyrenyl-1-ethynyl | succinimidyl ethynyl-phenyl pentanoate |
| 9 | pyrenyl-1-ethynyl | pyrenyl-1-ethynyl | propyl ethynyl-phenyl pentanamide |
| 10 | TMS—C≡ trimethylsilyl-1-ethynyl | pyrenyl-C≡C | CH₃— |
| 11 | H—C≡C— ethynyl | pyrenyl-C≡C | CH₃— |
| 12 | 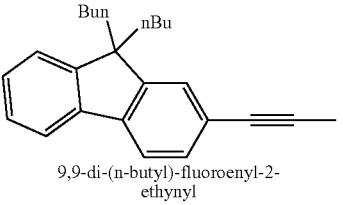 9,9-di-(n-butyl)-fluoroenyl-2-ethynyl | 9,9-di-(n-butyl)-fluorenyl-2-ethynyl | CH₃— |
| 13 | 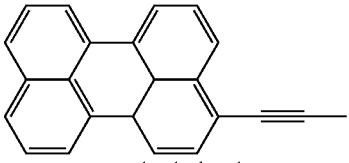 perylenyl-ethynyl | 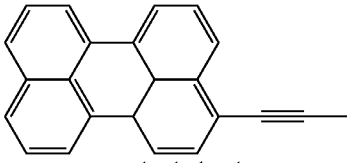 perylenyl-ethynyl | CH₃— |
| 14 | naphthyl-2-ethynyl | naphthyl-2-ethynyl | CH₃— |
| 15 | pyrenyl-1-ethynyl | pyrenyl-1-ethynyl | 4'-(2,2':6',2-terpyridine) |
| 16 | p-CH₃C₆H₄—C≡C-toluyl-1-ethynyl | 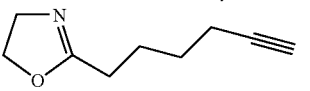 6-oxazoline-hex-1-inyl | methyl |
| 17 | pyrenyl-C≡C- | 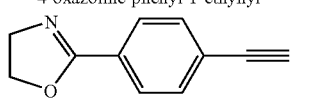 4-oxazoline-phenyl-1-ethynyl | p-iodo-phenyl |
| 18 | pyrenyl-1-ethynyl | pyrenyl-1-ethynyl | iodo-phenyl |
| 19 | pyrenyl-1-ethynyl | pyrenyl-1-ethynyl | ethynyl-phenyl-pentanoic acid |
| 20 | anthracenyl-9-ethynyl | anthracenyl-9-ethynyl | methyl |

EXAMPLE 1

Preparation of Compound 1

Compound 1 is prepared according to the following reaction pattern:

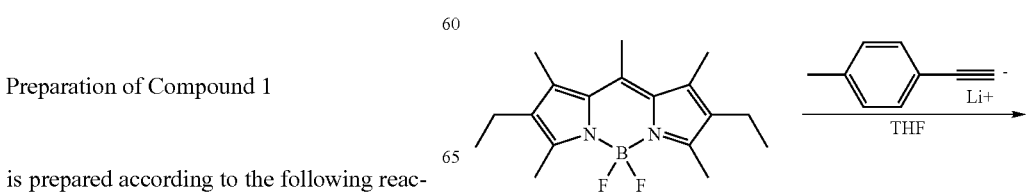

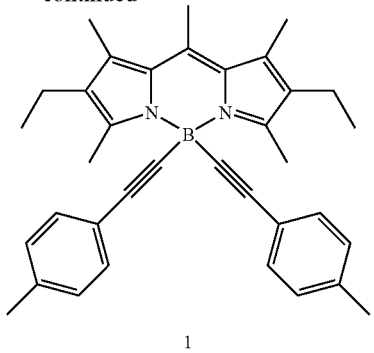

1

The starting material 4,4-difluoro-1,3,5,7,8-pentamethyl-2,6-diethyl-4-bora-3a,4a-diaza-s-indacene, used as difluoroboradipyrromethene, was prepared according to the following mode of operation. 1 g (12.7 mmol) of acetyl chloride and 0.67 g of 3-ethyl-2,4-dimethyl-pyrrole were introduced into anhydrous dichloromethane, and stirred at ambient temperature for 1 day. Subsequently, anhydrous petroleum ether was added and the precipitate obtained after stirring overnight was filtered and then dissolved in toluene. 1.6 ml of triethylamine (1.6 ml) were subsequently added, then 2 ml of $BF_3Et_2O$ (2 ml) were also added and the solution was heated to 80° C. for 15 minutes. After washing the organic phase (water 3×20 ml) and subjecting it to chromatography over silica gel (hexane/dichloromethane, 6:4), 0.5 g of compound 1' were obtained.

n-butyllithium (1.55 M in hexane, 0.44 ml) was added under argon to a solution of p-ethynyltoluene (80 μL, 0.63 mmol) in anhydrous THF at −78° C. The mixture was stirred for 1 hour at −78° C., then at ambient temperature for 30 minutes. The pale yellow solution thus obtained was transferred by cannula into a solution of difluoroboradipyrromethene 1' (100 mg, 0.31 mmol) in anhydrous THF. The solution was stirred for 5 minutes at ambient temperature, then water was added. Said solution was extracted with dichloromethane. After evaporation, the organic residue was purified by chromatography on a column of alumina ($CH_2Cl_2$/cyclohexane, 20:80), and compound 1 was obtained in the form of an orange powder (110 mg, 69%).

Characterisation of Compound 1

$^1H$ NMR ($CDCl_3$ 400 MHz): δ=7.28 (d, 4H, $^3J$=8.0 Hz), 7.0 (d, 4H, $^3J$=8.85 Hz), 2.84 (s, 6H), 2.63 (s, 3H), 2.45 (q, 4H, $^3J$=7.5 Hz) 2.37 (s, 6H), 2.30 (s, 6H), 1.1 (t, 6H, $^3J$=7.5 Hz);

$^{13}C$ NMR ($CDCl_3$, 75 MHz): 151.9, 139.6, 136.6, 134.2, 132.4, 131.8, 131.4, 130.1, 128.6, 122.6, 21.3, 17.5, 17.2, 15.1, 14.7, 13.9, $^{11}B$ NMR ($CDCl_3$, 128 MHz); −9.69 (s); UV-Vis ($CH_2Cl_2$) λ nm (ε, $M^{-1}$ $cm^{-1}$)=515 (68000), 371 (6600), 264 (45600), 252 (47100);

IR (KBr): ν=2963 (s), 2173 (m), 1555 (s), 1186 (s), 977 (s), 816 (s);

$FAB^+$ m/z: 511.2 ([M+H]+, 100);

Elemental analysis calculated for $C_{36}H_{39}BN_2$: C, 84.70; H, 7.70; N, 5.49. Found: C, 84.64; H, 7.62; N, 5.32.

FIG. 1 shows the structure of compound 1, obtained by single-crystal X-ray diffraction.

Figure 2:
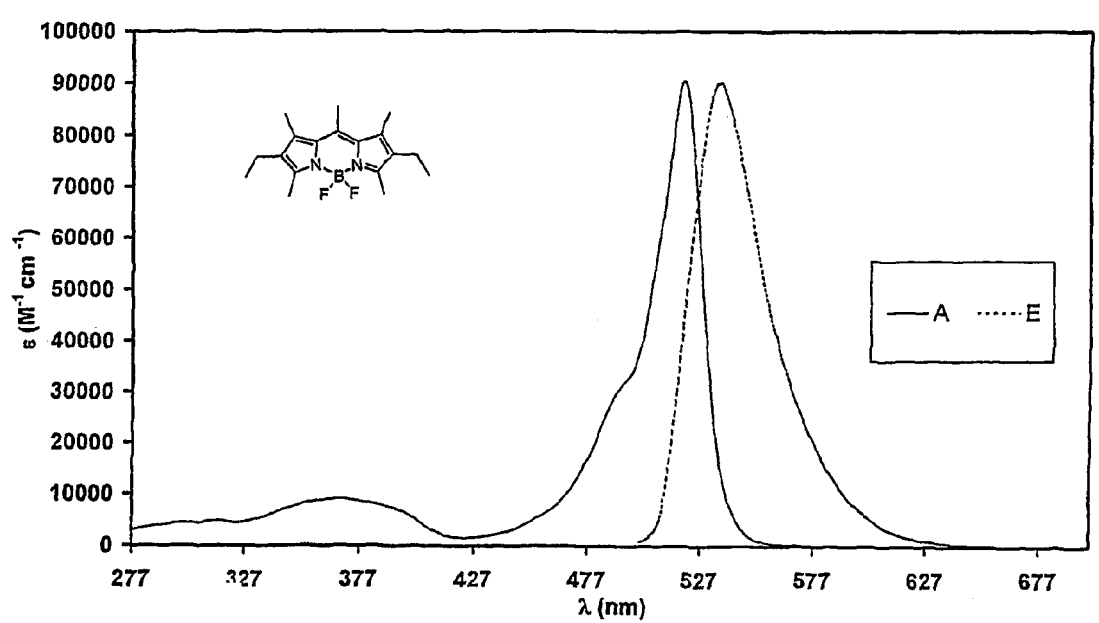
FIG. 2 shows the absorption spectrum (shown as a solid line, labelled A) and the emission spectrum (dotted line, labelled E) ($\lambda_{exc}$=515 nm) of the starting compound 4,4-difluoro-1,3,5,7,8-pentamethyl-2,6-diethyl-4-bora-3a,4a-diaza-s-indacene.

FIG. 2 shows the absorption spectrum (shown as a solid line, labelled A) and the emission spectrum (dotted line, labelled E) ($λ_{exc}$=515 nm) of the starting compound 4,4-difluoro-1,3,5,7,8-pentamethyl-2,6-diethyl-4-bora-3a,4a-diaza-s-indacene described in U.S. Pat. No. 5,446,157.

EXAMPLE 2

Preparation of Compound 2

Compound 2 is prepared according to the following reaction pattern:

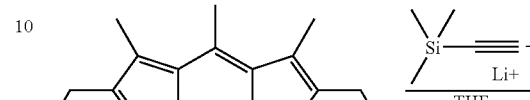

1'

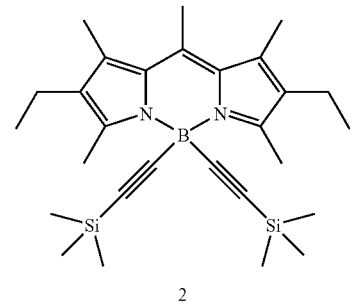

2

The difluoroboradipyrromethene 1' used as a starting material is identical to that of Example 1.

n-butyllithium (1.34 M in n-hexane, 0.94 ml) was added under argon to trimethylsilylacetylene (0.174 ml, 1.26 mmol) in anhydrous THF (10 ml) at −78° C. The mixture was subsequently stirred for 1 hour at −78° C., then stirred for 30 minutes at ambient temperature. The pale yellow solution was transferred by cannula into a solution of difluoroboradipyrromethene (0.2 g, 0.33 mmol) in anhydrous THF (40 ml). The solution was subsequently stirred at ambient temperature for 15 minutes until the starting material had completely disappeared (monitored by TLC). Water was added (10 ml) and the solution was extracted with $CH_2Cl_2$ (50 ml). After evaporation, the organic residue was purified by chromatography on a column of alumina ($CH_2Cl_2$/cyclohexane, 20:80), and was subsequently recrystallised in a $CH_2Cl_2$/hexane mixture in order to obtain the pure compound 3 (0.21 g, 70%).

Characterisation of Compound 2

$^1H$ NMR ($CDCl_3$ 300 MHz): δ=2.67 (s, 6H), 2.58 (s, 3H), 2.43 (q, 4H, $^3J$=7.5 Hz), 2.34 (s, 6H), 1.05 (t, 6H, $^3J$=7.5 Hz), 0.09 (s, 6H);

$^{13}C\{1H\}$ NMR ($CDCl_3$, 75 MHz): δ=152.0, 139.5, 134.1, 132.4, 130.1, 17.6, 17.3, 15.2, 14.8, 13.9, 0.5;

$^{11}B$ NMR ($CDCl_3$, 128 MHz); −11.10 (s);

UV-Vis ($CH_2Cl_2$) λnm (ε, $M^{-1}cm^{-1}$)=516 (42700), 366 (3500), 278 (24000).

EXAMPLE 3

Preparation of Compound 3

Compound 3 was prepared according to the following reaction pattern 3.

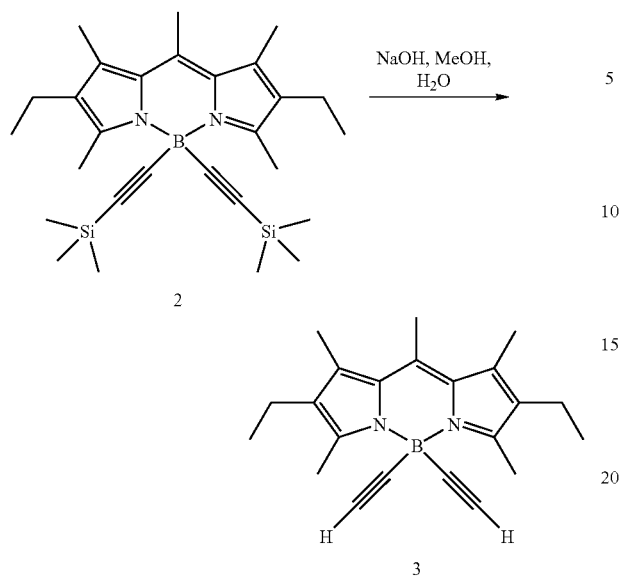

A sodium hydroxide solution (345 mg, 20 eq in 5 ml of methanol) was added to a solution of compound 2 (210 mg, 0.43 mmol) in 5 ml of $CH_2Cl_2$. The mixture was stirred for two days at ambient temperature until the starting material had completely disappeared. Water (10 ml) was subsequently added, and the solution was extracted with $CH_2Cl_2$ (50 ml). After evaporation, the organic material was purified by chromatography on a column of silica ($CH_2Cl_2$/cyclohexane, 30:70), and was then recrystallised in $CH_2Cl_2$/hexane. Pure compound 4 was obtained in the form of orange-coloured crystals (92 mg, 60%);

$^1$H NMR ($CDCl_3$ 300 MHz): δ=2.72 (s, 6H), 2.61 (s, 3H), 2.43 (q, 4H, $^3J$=7.5 Hz), 2.34 (s, 6H), 2.17 (s, 2H), 1.06 (t, 6H, $^3J$=7.5 Hz); $^{13}C$ {$^1H$} NMR ($CDCl_3$, 75 MHz): δ=151.9, 139.8, 134.8, 132.7, 130.2, 17.5, 17.4, 15.1, 14.8, 14.0;

$^{11}B$ NMR ($CDCl_3$, 128 MHz); −11.05 (s); UV-Vis ($CH_2Cl_2$) λnm (ϵ, $M^{-1}$ $cm^{-1}$)=514 (80000), 367 (5100), 280 (10100), 245 (15600).

Figure 3:
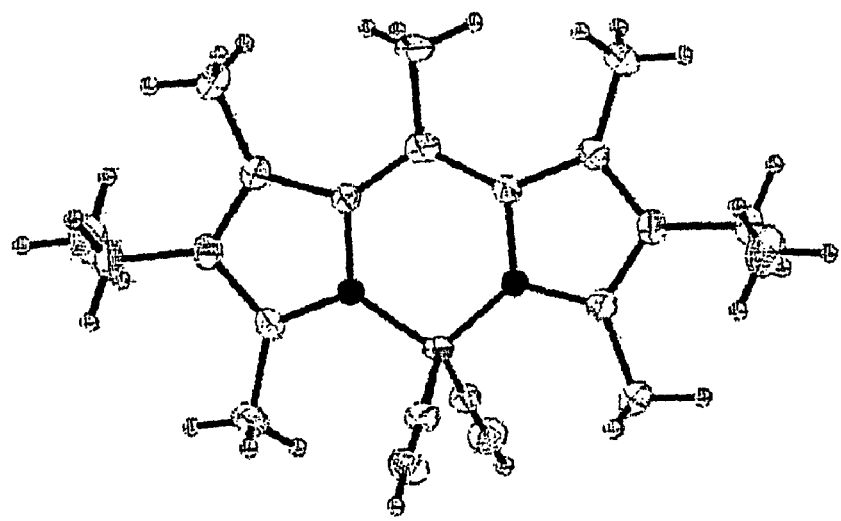
FIG. 3 shows the structure of compound 4, obtained by single-crystal X-ray diffraction.

FIG. 3 shows the structure of compound 4, obtained by single-crystal X-ray diffraction.

EXAMPLE 4

Preparation of Compound 4

Compound 4 is prepared according to the following reaction pattern

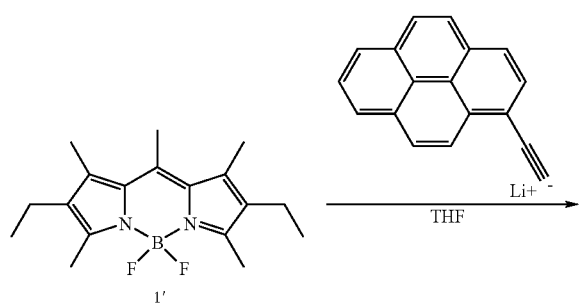

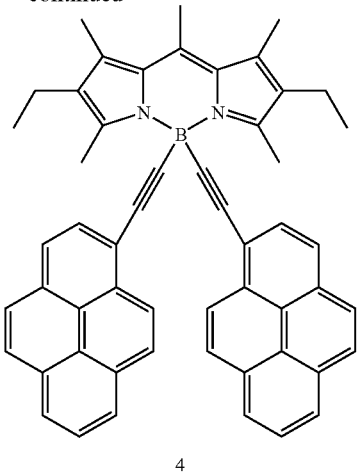

n-butyllithium (1.55 M in hexane, 0.44 ml) was added to a solution of 1-ethynylpyrene (142 mg, 0.63 mmol) in anhydrous THF under argon at −78° C. The mixture was stirred for 1 hour at −78° C., and then stirred for 30 minutes at ambient temperature. The solution thus obtained was transferred by cannula into a solution of 4,4-difluoro-1,3,5,7,8-pentamethyl-2,6-diethyl-4-bora-3a,4a-diaza-s-indacene (100 mg, 0.31 mmol) in anhydrous THF (20 ml). The solution was stirred for 30 minutes at ambient temperature until the starting material had disappeared (monitored by TLC), then water was added. Said solution was extracted with dichloromethane. After evaporation, the organic residue was purified by chromatography on a column of alumina ($CH_2Cl_2$/cyclohexane, 20:80), and was then recrystallised in a $CH_2Cl_2$/cyclohexane mixture in order to obtain compound 5 in the form of orange-coloured crystals (76 g, 30%).

Characterisation of Compound 4

$^1$H NMR ($CDCl_3$ 400 MHz): δ=8.75 (d, 2H, $^3J$=9.0 Hz), 8.16-7.96 (m, 16H), 3.11 (s, 6H), 2.74 (s, 3H), 2.56 (q, 4H, $^3J$=7.5 Hz), 2.45 (s, 6H), 1.17 (t, 6H, $^3J$=7.5 Hz);

$^{13}$C NMR ($CDCl_3$, 100 MHz): 152.1, 140.0, 134.7, 132.8, 132.1, 131.4, 131.3, 130.5, 130.4, 129.7, 127.8, 127.43, 127.38, 126.4, 126.0, 125.3, 125.11, 125.08, 124.61, 124.57, 124.4, 94.4, 17.6, 17.4, 15.2, 14.8, 14.5;

$^{11}$B NMR ($CDCl_3$, 128 MHz): −16.8 (s); UV-Vis ($CH_2Cl_2$) λnm (ϵ, $M^{-1}$ $cm^{-1}$)=516 (73000), 371 (95000), 350 (69000), 286 (93000), 275 (53000), 248 (86000), 241 (80500);

IR (KBr): ν=2960 (s), 2293 (m), 1599 (s), 1430 (s), 1184 (s), 978 (s);

FAB$^+$ m/z: 731.2 ([M+H]$^+$, 100), 505.2 ([M-pyr-≡]$^+$, 25);

Elemental analysis calculated for $C_{54}H_{43}BN_2$: C, 88.76; H, 5.93; N, 3.83. Found: C, 88.57; H, 5.77; N, 3.65.

Figure 4:
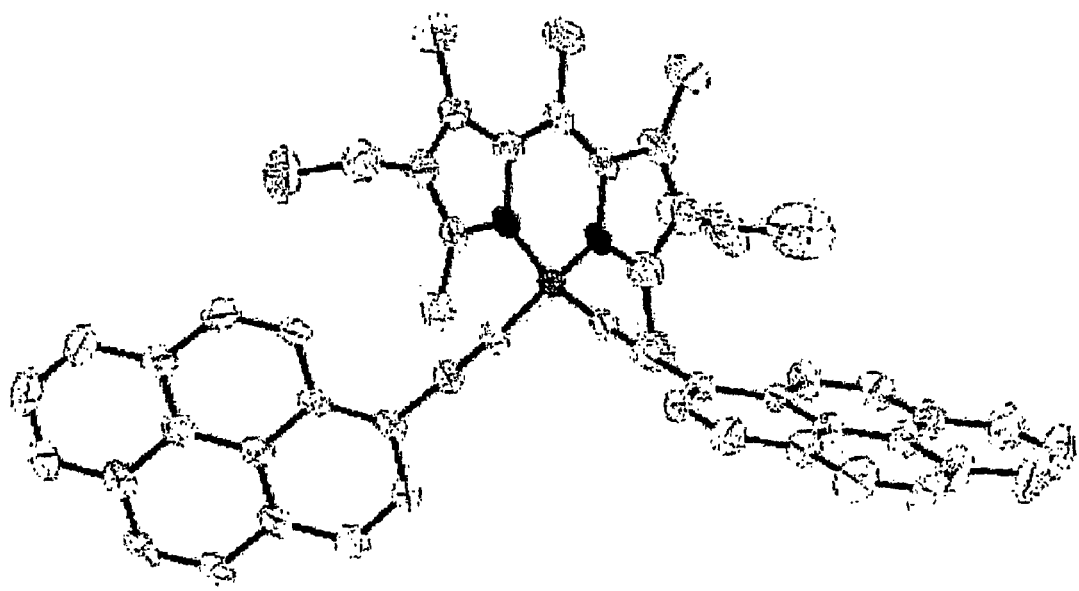
FIG. 4 shows the structure of compound 4, obtained by single-crystal X-ray diffraction.

FIG. 4 shows the structure of compound 4, obtained by single-crystal X-ray diffraction.

Figure 5:
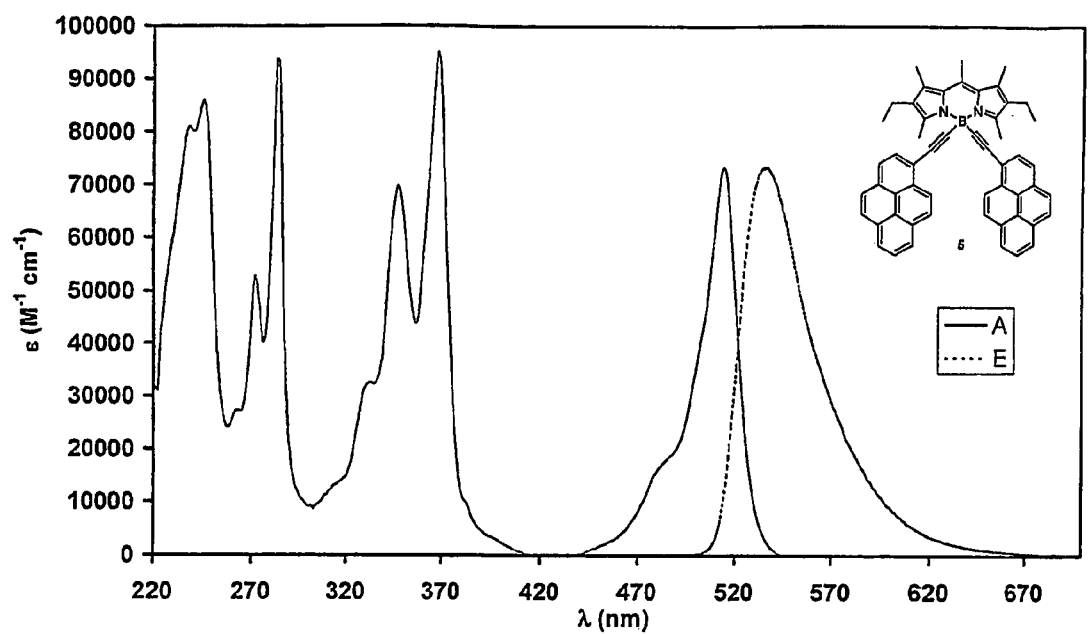
FIG. 5 shows the absorption spectrum (solid line, labelled A) and the emission spectrum (dotted line, labelled E) ($\lambda_{exc}$=515 nm) of compound 4.

FIG. 5 shows the absorption spectrum (solid line, labelled A) and the emission spectrum (dotted line, labelled E) ($λ_{exc}$=515 nm) of compound 4.

Figure 6:
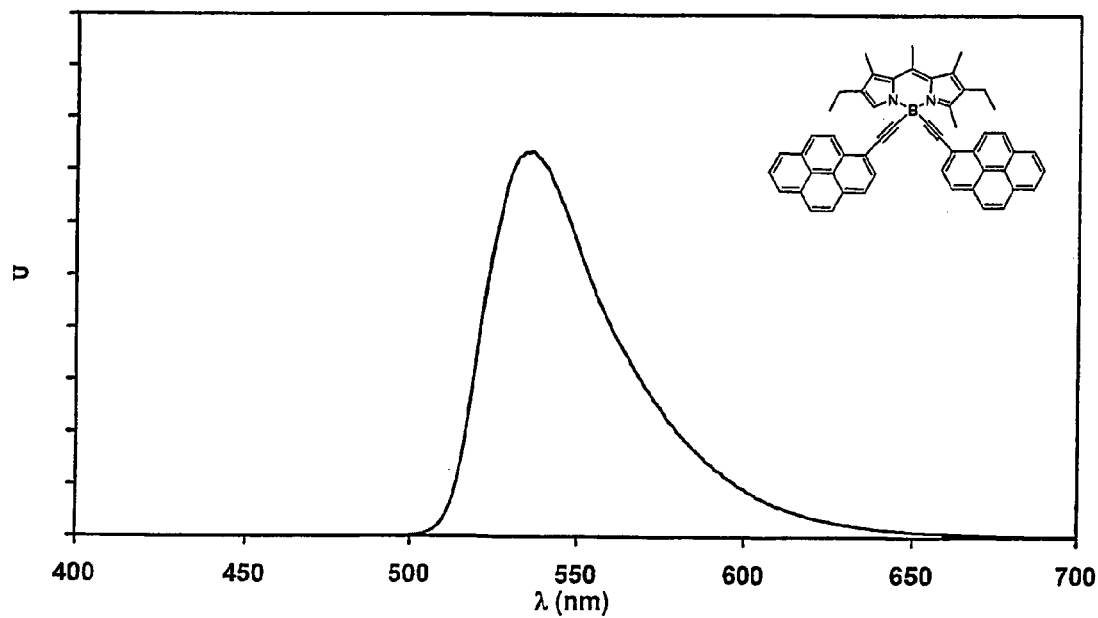
FIG. 6 shows the emission spectrum of compound 4 with $\lambda_{exc}$ at 370 nm, and a quantum yield of 94%.

FIG. 6 shows the emission spectrum of compound 4 with $λ_{exc}$ at 370 nm, and a quantum yield of 94%.

EXAMPLE 5

Preparation of Compound 5

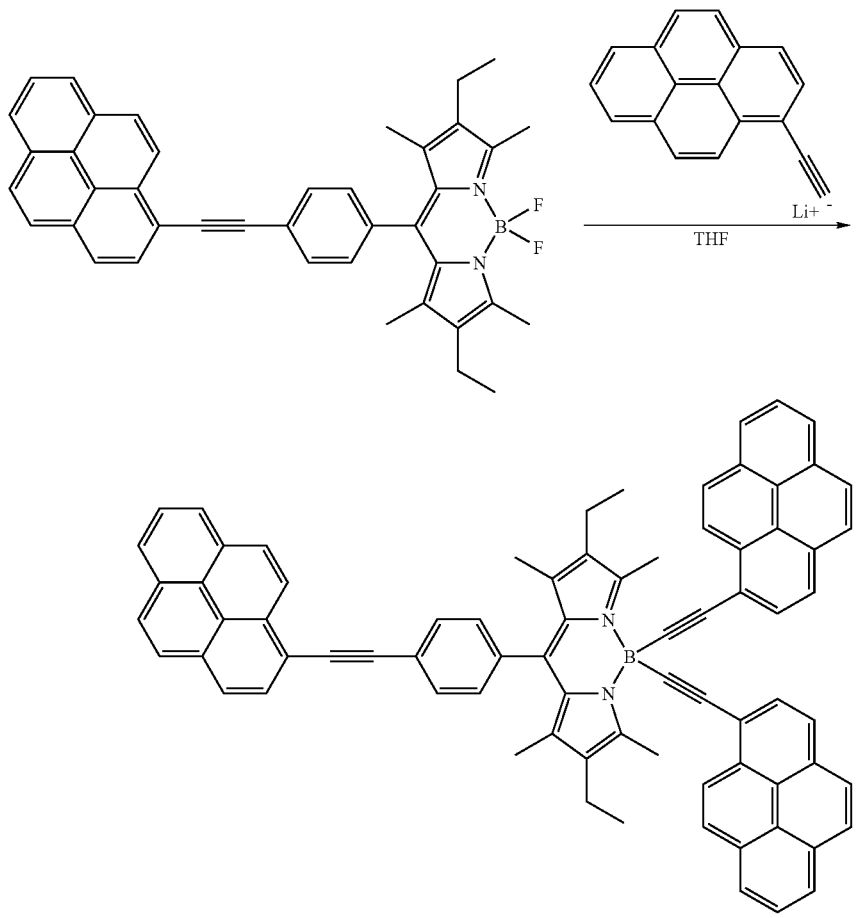

4,4-difluoro-8-((1-pyrenylethynyl)-4-phenyl)-1,3,5,7-tetramethyl-2,6-diethyl-4-bora-3a,4a-diaza-s-indacene was prepared by a Sonogashira coupling between 1-ethynylpyrene and 4,4-difluoro-1,3,5,7-tetramethyl-8-(p-iodophenyl)-2,6-diethyl-4-bora-3a,4a-diaza-s-indacene 2' according to the following mode of operation. 2 g (7.5 mmol) of p-iodobenzoyle chloride and 2.24 ml (16.5 mmol) of 3-ethyl-2,4-dimethyl-pyrrole were stirred for one day at 40° C. Subsequently, 6.9 ml of triethylamine and 7.6 ml of $BF_3Et_2O$ were added. The mixture was stirred overnight, and the organic phase was subsequently washed with water. 1.2 g of compound 2' was obtained by chromatography over alumina (hexane/dichloromethane, 7:3) and recrystallisation in a hexane/dichloromethane mixture.

n-butyllithium (1.55 M in n-hexane, 0.11 ml) was added to a solution of 1-ethynylpyrene (37 mg, 0.17 mmol) in anhydrous THF (10 ml), under argon at −78° C. The mixture was stirred for one hour at −78° C., then at ambient temperature for 30 minutes. The dark green solution was then transferred by cannula into a solution of 4,4-difluoro-8-((1-pyrenylethynyl)-4-phenyl)-1,3,5,7-tetramethyl-2,6-diethyl-4-bora-3a,4a-diaza-s-indacene (50 mg, 0.085 mmol) in anhydrous THF (20 ml). The solution was stirred at ambient temperature for 30 minutes until the starting material had entirely disappeared (monitored by TLC). Water (5 ml) was then added, and the solution was extracted with $CH_2Cl_2$ (20 ml). After evaporation, the organic residue was purified by chromatography on a column of alumina ($CH_2Cl_2$/cyclohexane, 30:70), and was then recrystallised in a $CH_2Cl_2$/hexane mixture in order to obtain compound 5 (43 mg, 20%).

Characterisation of Compound 5

$^1$H NMR (CDCl$_3$ 400 MHz): δ=8.84 (d, 2H, $^3$J=8.9 Hz), 8.76 (d, 1H, $^3$J=8.9 Hz), 8.30-8.00 (m, 25H), 7.94 (d, 2H, $^3$J=8.0 Hz), 3.21 (s, 6H), 2.52 (q, 4H, $^3$J=7.5 Hz), 1.56 (s, 6H), 1.67 (t, 6H, $^3$J=7.5 Hz);

$^{13}$C NMR (CDCl$_3$, 100 MHz): 154.2, 139.6, 136.7, 136.5, 133.3, 132.3, 132.1, 132.0, 131.5, 131.4, 131.3, 131.2, 131.1, 130.4, 129.71, 129.67, 129.2, 129.0, 128.5, 128.3, 127.8, 127.5, 127.35, 127.27, 126.33, 126.28, 126.0, 125.77, 125.72, 125.5, 125.1, 124.60, 124.56, 124.5, 124.42, 124.36, 124.0, 120.5, 117.4, 94.7, 89.8, 17.5, 14.9, 14.6, 12.3;

$^{11}$B NMR (CDCl$_3$, 128 MHz); −8.91 (s);

UV-Vis ($CH_2Cl_2$) λnm (ε, M$^{-1}$ cm$^{-1}$)=523 (72600), 370 (138400), 351 (99000), 285 (133000), 275 (97000), 248 (118300);

IR (KBr): ν=2926 (s), 2169 (m), 1542 (s), 1402 (s), 1179 (s), 843 (s); IR (KBr): ν=3118 (m), 2926 (s), 2169 (m), 1542 (s), 1402 (s), 1179 (s), 978 (s), 843 (s), 757 (s);

FAB$^+$ m/z: 1017.2 ([M+H]$^+$, 90), 791.1 ([M-pyr-≡]$^+$, 20;

Elemental analysis calculated for $C_{77}H_{53}BN_2$: C, 90.9; H, 5.2; N, 2.75. Found: C, 90.6; H, 4.9; N, 2.48.

EXAMPLE 6

Preparation of Compound 6

Compound 6 is prepared according to the following reaction pattern

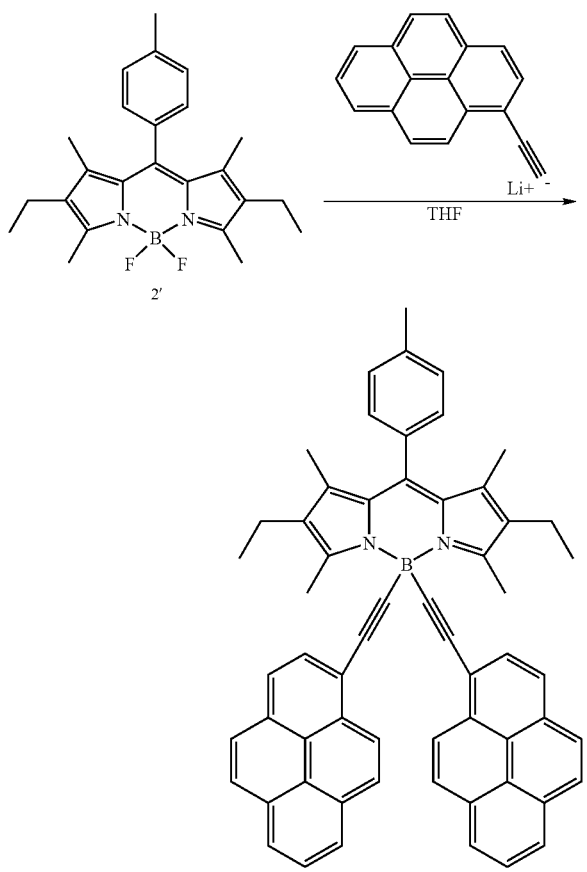

The 4,4-difluoro-1,3,5,7-tetramethyl-8-(p-iodophenyl)-2,6-diethyl-4-bora-3a,4a-diaza-s-indacene 2' was prepared according to the following mode of operation.

n-butyllithium (1.55 M in hexane, 0.26 ml) was added to a solution of 1-ethynylpyrene (89 mg, 0.39 mmol) in anhydrous THF (10 ml) under argon at −78° C. The mixture was stirred for 1 hour at −78° C., then at ambient temperature for 30 minutes. The dark green solution thus obtained was transferred by cannula into a solution of 4,4-difluoro-1,3,5,7-tetramethyl-8-(p-iodophenyl)-2,6-diethyl-4-bora-3a,4a-diaza-s- indacene 2' (100 mg, 0.19 mmol) in anhydrous THF (20 ml). The solution was stirred for 15 minutes at ambient temperature until the starting material had disappeared (monitored by TLC), then water was added (10 ml). Said solution was extracted with dichloromethane (20 ml). After evaporation, the organic residue was purified by chromatography on a column of alumina ($CH_2Cl_2$/cyclohexane, with a gradient of from 90:10 to 70:30), and was then recrystallised in a $CH_2Cl_2$/cyclohexane mixture in order to obtain compound 6 in the form of orange crystals (132 mg, 76%).

Characterisation of Compound 6

$^1$H NMR ($CDCl_3$ 400 MHz): δ=8.78 (d, 2H, $^3J$=9.0 Hz), 8.17-7.97 (m, 16H), 7.88 (d, 2H, $^3J$=8.5 Hz), 7.22 (d, 2H, $^3J$=8.5 Hz), 3.16 (s, 6H), 2.47 (q, 4H, $^3J$=7.5 Hz), 1.44 (s, 6H), 1.11 (t, 6H, $^3J$=7.5 Hz);

$^{13}$C NMR ($CDCl_3$, 75 MHz): 154.3, 138.8, 138.2, 136.3, 136.1, 133.4, 132.1, 131.3, 131.2, 130.7, 130.4, 129.6, 129.1, 127.8, 127.5, 127.3, 126.2, 126.0, 125.1, 124.6, 124.5, 124.4, 120.4, 94.5, 17.7, 15.1, 14.8, 12.5;

$^{11}$B NMR ($CDCl_3$, 128 MHz); −8.92 (s);

UV-Vis ($CH_2Cl_2$) λnm (ε, $M^{-1}$ $cm^{-1}$)=523 (70300), 370 (95000), 350 (72100), 285 (94000), 274 (56000), 247 (89700);

$FAB^+$ m/z: 919.1 ($[M+H]^+$, 100), 693.2 ($[M-pyr-≡]^+$, 32);

Elemental analysis calculated for $C_{59}H_{44}BIN_2$: C, 77.13; H, 4.83; N, 3.05. Found: C, 76.81; H, 4.51; N, 2.75.

EXAMPLE 8

Preparation of Compound 7

Compound 7 was prepared according to the following reaction pattern:

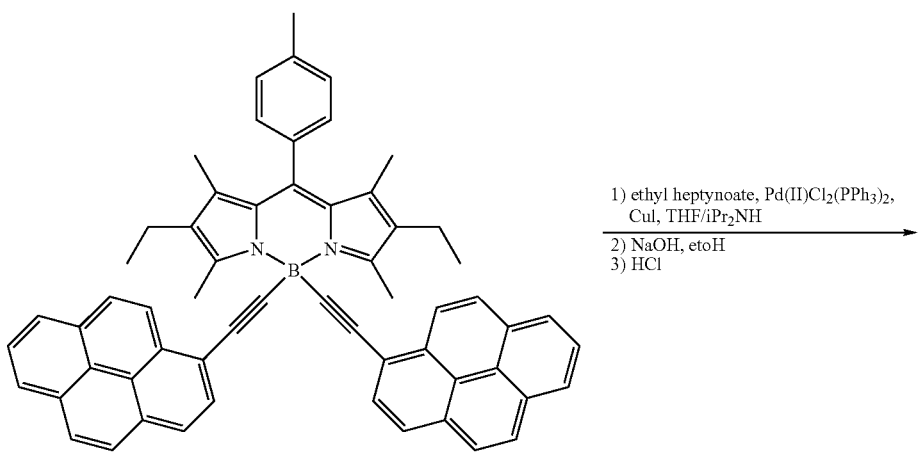

-continued

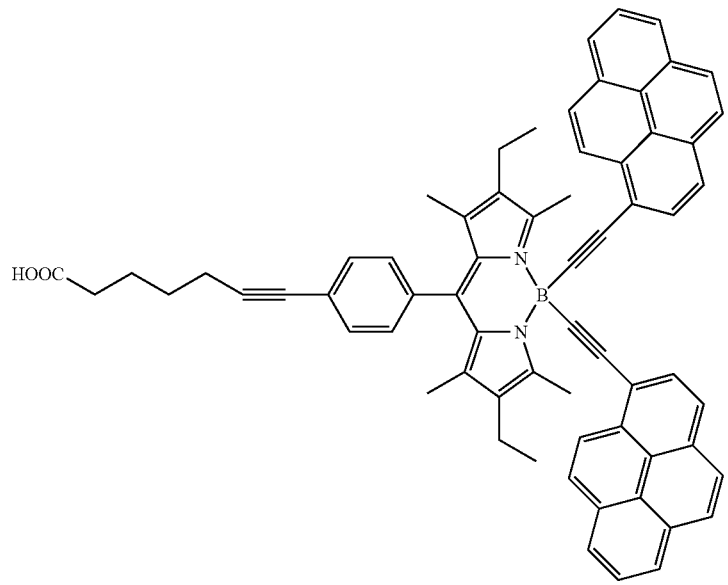

8

A solution of compound 6 (0.1 g, 0.110 mmol) and heptynoic ester (0.025 g, 0.165 mmol) was degassed for 30 minutes in a THF/iPr$_2$NH (10/1.5 ml) mixture. Pd (II) Cl$_2$ (PPh$_3$)$_2$ (4 mg, 6 mole %) and CuI (2 mg, 10 mole %) were subsequently added and the mixture was stirred at ambient temperature for 16 hours. After the reaction had finished, 50 ml of water were added and the organic phases were extracted with CH$_2$Cl$_2$ (30 ml) and then dried with MgSO$_4$. The ester was obtained after purification on a chromatography column over alumina (eluant: cyclohexane/CH$_2$Cl$_2$ 80:30) followed by recrystallisation in CH$_2$Cl$_2$/hexane (amount obtained: 0.09 g, 91%). The ester was subsequently heated for 12 hours at 60° C. in an EtOH/THF solution (10/10 ml) in the presence of an excess of 1 M NaOH solution (9.7 ml, 1 mmol). A diluted hydrochloric acid solution was added to lower the pH to 4, which led to precipitation of the desired acid. The product was then extracted with CH$_2$Cl$_2$ (50 ml) and washed twice with water (50 ml), then dried with MgSO$_4$. Pure acid was obtained after recrystallisation of the product in CH$_2$Cl$_2$/hexane (79 mg, 87% yield).

Characterisation of Compound 7

$^1$H NMR (CDCl$_3$ 300 MHz): 8.77 (d, 2H, $^3$J=9.0 Hz), 8.17-7.96 (m, 16H), 7.56 (d, 2H, $^3$J 8.3 Hz), 7.38 (d, 2H, $^3$J=8.3 Hz), 3.14 (s, 6H), 2.53-2.41 (m, 8H), 1.96-1.83 (m, 2H), 1.77-1.63 (m, 2H), 1.42 (s, 6H), 1.07 (t, 6H, $^3$J=7.6 Hz);

$^{13}$C NMR (CDCl$_3$, 75 MHz):154.2, 139.9, 136.7, 136.0, 134.8, 133.3, 132.3, 132.2, 131.5, 131.3, 130.5, 129.8, 129.3, 128.8, 127.9, 127.6, 127.5, 126.4, 124.7, 124.6, 124.5, 124.4, 120.6, 33.3, 28.1, 19.4, 17.6, 15.0, 14.7, 12.3;

$^{11}$B NMR (CDCl$_3$, 128 MHz); −8.92 (s);

UV-Vis (CH$_2$Cl$_2$) λnm (ε, M$^{-1}$ cm$^{-1}$)=523 (58100), 370 (75000), 350 (66400), 285 (67200), 274 (56300), 251 (67600);

IR (KBr): ν=2962 (s), 2164 (m), 1633 (s), 1544 (s), 1180 (s), 977 (s), 846 (s);

FAB$^+$ m/z (nature of peak, relative intensity): 917.2 ([M−OH]$^+$, 25);

Elemental analysis calculated for C$_{67}$H$_{a7}$BN$_2$O$_2$, HCl: C, 83.01; H, 6.03; N, 2.89. Found: C, 83.08; H, 5.95; N, 2.88.

EXAMPLE 8

Compound 9 has an activated acidic group allowing the compound to be grafted on a protein or another biomolecule containing amino residues.

Preparation of Compound 8

Compound 8 was prepared according to the following reaction pattern:

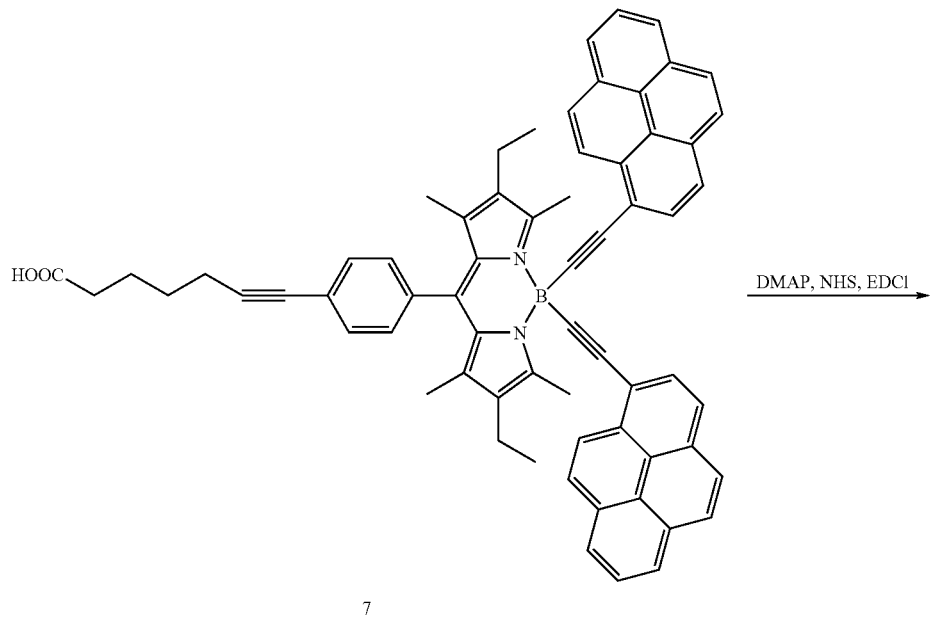

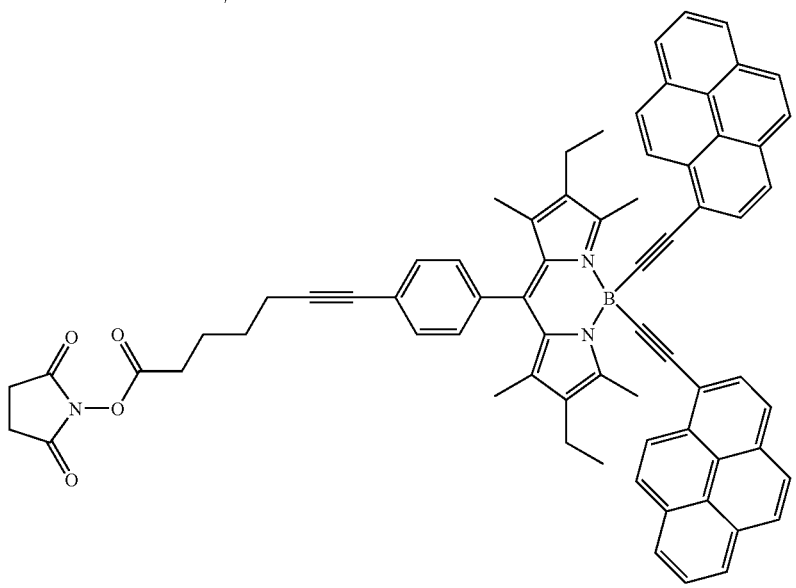

Acid 7 (30 mg g, 0.033 mmol) in 10 ml of $CH_2Cl_2$ was added in the presence of dimethylaminopyridine (8.4 mg, 0.066 mmol), EDCI (12 mg, 0.066 mmol) and N-hydroxysuccinimide (7.2 mg, 0.066 mmol). The mixture was stirred at ambient temperature, and the reaction was monitored by TLC plate. After compound 8 had completely disappeared (1 hour), the mixture was washed with water (10 ml), and then dried over $MgSO_4$. The pure product was obtained after purification by a chromatography column over silica (eluant: $CH_2Cl_2$) followed by recrystallisation in $CH_2Cl_2$/hexane (amount obtained: 0.018 g, 54%).

Characterisation of Compound 8

$^1$H NMR ($CDCl_3$ 300 MHz): 8.78 (d, 2H, $^3J$=9.1 Hz), 8.17-7.96 (m, 16H), 7.56 (d, 2H, $^3J$=8.3 Hz), 7.39 (d, 2H, $^3J$=8.3 Hz), 3.14 (s, 6H), 2.9 (s, 4H), 2.73 (t, 2H, $^3J$=7.1 Hz), 2.53 (q, 4H, $^3J$=7.5 Hz), 2.04-1.94 (m, 2H), 1.82-1.73 (m, 2H), 1.43 (s, 6H), 1.10 (t, 6H, $^3J$=7.5 Hz);

$^{13}$C NMR ($CDCl_3$, 75 MHz): 169.2, 168.2, 154.2, 136.7, 136.0, 133.3, 132.35, 132.34, 132.28, 131.8, 131.5, 130.5, 129.8, 129.4, 128.9, 127.9, 127.6, 127.5, 126.4, 126.1, 125.2, 124.8, 124.7, 124.5, 124.3, 120.7, 90.5, 30.7, 27.8; 25.8, 24.0, 19.2, 17.6, 15.0, 14.7, 12.3;

$^{11}$B NMR ($CDCl_3$, 128 MHz); −8.97 (s);

UV-Vis ($CH_2Cl_2$) λnm (ε, $M^{-1}$ $cm^{-1}$)=523 (55000), 370 (70000), 350 (56000), 285 (81000), 274 (57000), 248 (88000);

IR (KBr): ε=3435 (m), 2960 (s), 2927 (s), 2230 (m), 2169 (m), 1741 (s), 1543 (s) 1431 (s), 1180 (s), 978 (s), 848 (s);

Elemental analysis calculated for $C_{70}H_{56}BN_3O_4 \cdot CH_2Cl_2$: C, 77.60; H, 5.32; N, 3.82. Found: C, 77.54; H, 5.28; N, 3.72.

Figure 7:
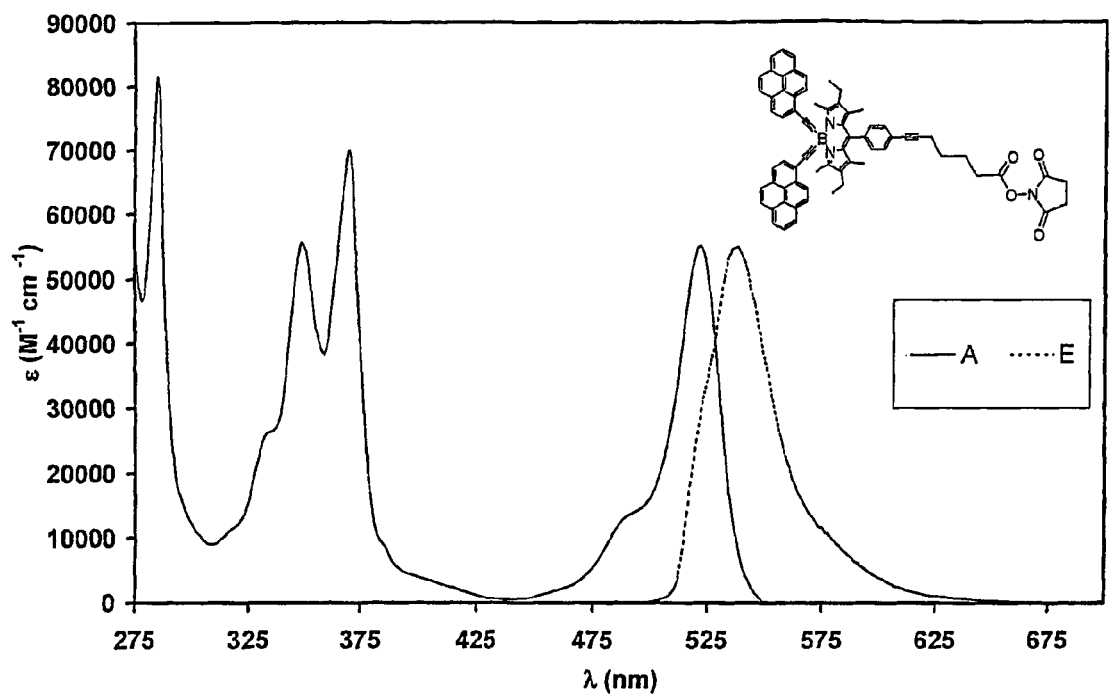
FIG. 7 shows the absorption spectrum (solid line, labelled A) and the emission spectrum (dotted line, labelled E) ($\lambda_{exc}$=515 nm) of compound 9.

FIG. 7 shows the absorption spectrum (solid line, labelled A) and the emission spectrum (dotted line, labelled E) ($\mu_{exc}$=515 nm) of compound 9.

Figure 8:
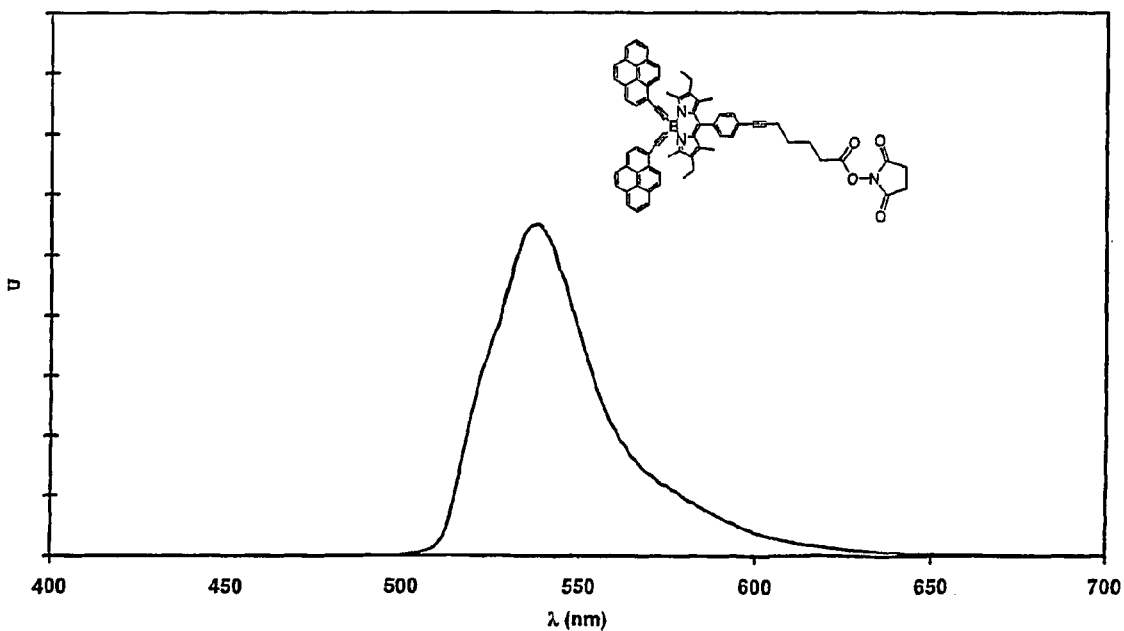
FIG. 8 shows the emission spectrum of compound 8 with $\lambda_{exc}$ at 372 nm, and a quantum yield of 98%.

FIG. 8 shows the emission spectrum of compound 8 with $\lambda_{exc}$ at 372 nm, and a quantum yield of 98%.

EXAMPLE 9

Preparation of Compound 9

The method of preparing compound 9 shows the reaction of a functional group G particular to a compound according to the invention, with an amino group which could be a that of a protein (a lysine, for example) or a modified oligonucleotide which could be labelled using a compound according to the present invention. For example, binding a specific protein to the compound according to the present invention allows biological receptors specific to that protein to be detected.

Compound 9 was prepared according to the following reaction pattern:

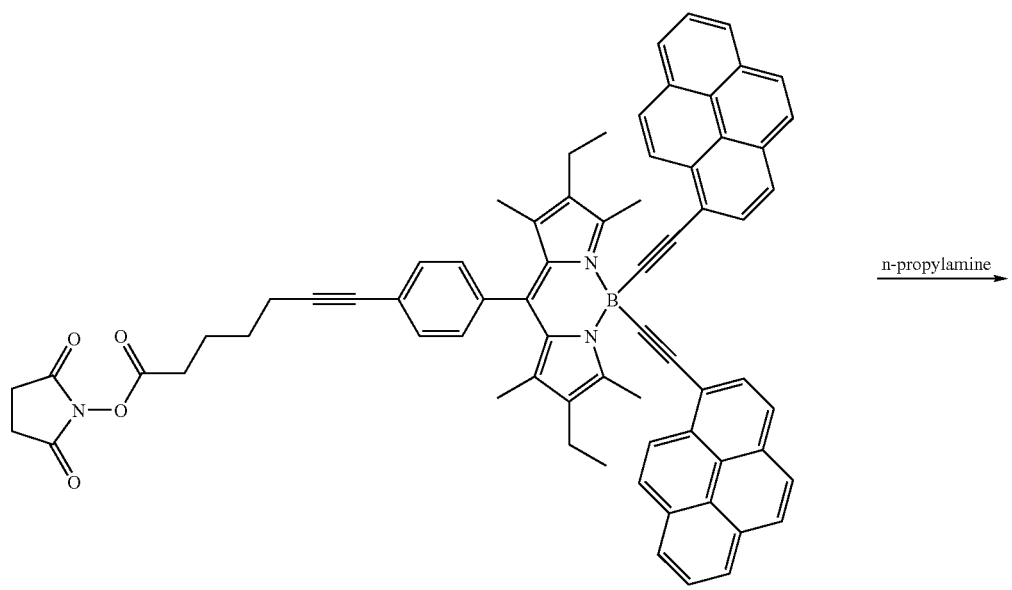

8

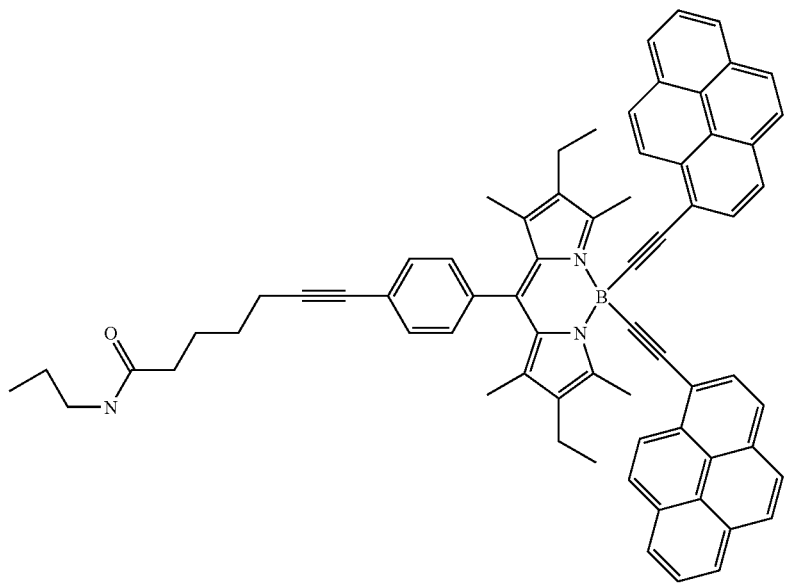

9

Compound 8 (10 mg, 0.0099 mmol) was stirred for one hour in 10 ml of n-propylamine; the solvent was subsequently evaporated and the resulting solid was extracted with $CH_2Cl_2$ (20 ml), then washed twice with water (20 ml). The pure product was obtained after purification by a chromatography column over silica (eluant gradient: $CH_2Cl_2$/MeOH from 100/0 to 95/5) (7 mg, 74%).

Characterisation of Compound 9

$^1$H NMR ($CDCl_3$, 300 MHz): 8.78 (d, 2H, $^3J$=9.0 Hz), 8.17-7.96 (m, 16H), 7.56 (d, 2H, $^3J$=8.3 Hz), 7.38 (d, 2H, $^3J$=8.3 Hz), 3.27 (m, 2H), 3.14 (s, 6H), 2.52-2.42 (m, 6H), 2.25 (t, 2H, $^3J$=7.2 Hz), 1.98-1.85 (m, 2H), 1.74-1.66 (m, 2H), 1.53 (q, 2H, $^3J$=7.2 Hz), 1.42 (s, 6H), 1.10 (t, 6H, $^3J$=7.4 Hz), 0.93 (t, 3H, $^3J$=7.4 Hz);

$^{13}$C NMR ($CDCl_3$, 75 MHz): 172.7, 154.2, 139.9, 136.6, 136.0, 133.3, 132.29, 132.27, 131.5, 131.3, 130.5, 129.8, 129.3, 128.8, 127.9, 127.6, 127.5, 126.4, 126.1, 125.3, 124.7, 124.6, 124.5, 124.4, 120.6, 91.1, 41.4, 36.5, 28.4, 25.2, 23.2, 19.4, 17.6, 15.0, 14.7, 12.3, 11.5;

$^{11}$B NMR ($CDCl_3$, 128 MHz); -8.97 (s).

UV-Vis ($CH_2Cl_2$) λnm (ε, $M^{-1}$ $cm^{14}$)=523 (60700), 370 (88000), 350 (70000), 285 (91000), 274 (57000), 248 (103000); ν=2962 (s), 2317 (m), 2172 (s) 1711 (m), 1648 (s), 1543 (s), 1180 (s), 847 (s);

$FAB^+$ m/z (nature of peak, relative intensity): 958.2 ($[M]^+$, 100);

Elemental analysis calculated for $C_{69}H_{60}BN_3O\cdot CH_2Cl_2$: C, 80.61; H, 5.99; N, 4.03. Found: C, 80.44; H, 5.87; N, 3.85.

EXAMPLE 10

Preparation of Compound 10

Compound 10 was prepared according to the following reaction pattern.

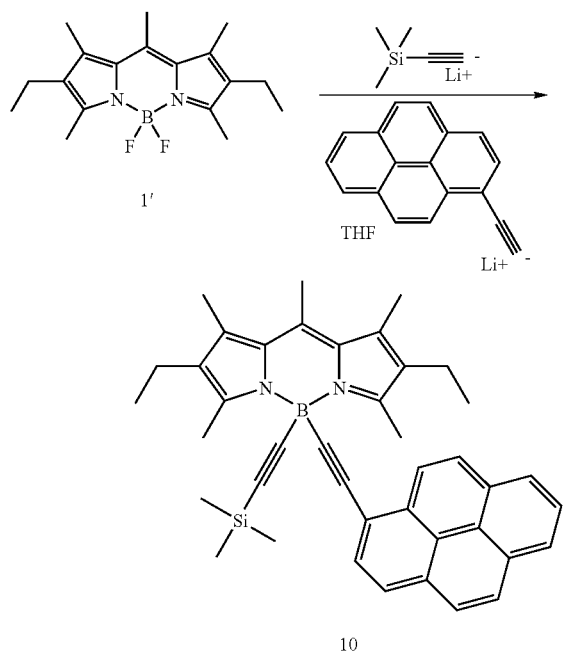

1-ethynylpyrene (71 mg, 0.31 mmol, 1 eq) and trimethylsilylacetylene (87 μL, 0.32 mmol, 1 eq) were put in two different Schlenk tubes, each containing 5 ml of anhydrous THF, and then n-butyllithium (1.34 M, 0.23 ml) was added to each of the tubes at −78° C. The two solutions were then kept at −78° C. for one hour and at ambient temperature for 30 minutes. The two solutions were simultaneously transferred by cannula into a solution of 4,4-difluoro-1,3,5,7,8-pentamethyl-2,6-diéthyl-4-bora-3a,4a-diaza-s-indacene 1' (100 mg, 0.31 mmol) in anhydrous THF (20 ml). The solution was subsequently stirred at ambient temperature for 10 minutes until the starting material had completely disappeared. Water was then added (5 ml) and the solution was extracted with $CH_2Cl_2$ (20 ml). After evaporation of the solvent, the organic residue was purified by chromatography on a column of silica ($CH_2Cl_2$/cyclohexane, 20:80). After recrystallisation in $CH_2Cl_2$/hexane, compound 10 (47 mg, 25%) was obtained.

Characterisation of Compound 10

$^1$H NMR ($CDCl_3$ 400 MHz): δ=8.62 (d, 1H, $^3J$=9.1 Hz), 8.17-8.13 (m, 2H), 8.09-7.95 (m, 6H), 2.90 (s, 6H), 2.65 (s, 3H), 2.49 (q, 4H, $^3J$=7.5 Hz), 2.38 (s, 6H), 1.12 (t, 6H, $^3J$=7.5 Hz), 0.18 (s, 9H);

$^{13}$C NMR ($CDCl_3$, 100 MHz): 152.1, 139.8, 134.5, 132.7, 132.3, 131.5, 131.3, 130.4, 130.3, 129.6, 127.7, 127.5, 126.4, 126.1, 125.1, 124.6, 124.4, 120.8, 17.6, 17.4, 15.2, 14.8, 14.3, 0.6;

$^{11}$B NMR ($CDCl_3$, 128 MHz): -10.2 (s);

UV-Vis ($CH_2Cl_2$) λnm (ε, $M^{-1}$ $cm^{-1}$)=515 (44200), 368 (30300), 349 (22600), 333 (11200), 285 (31400), 274 (18200), 248 (29000), 242 (28200).

EXAMPLE 11

Compound 11 is a compound which has a true acetylenic group $S^i$ which can be coupled with an aromatic halide by Sonogashira coupling with palladium.

Preparation of Compound 11

Compound 11 was prepared according to the following reaction pattern.

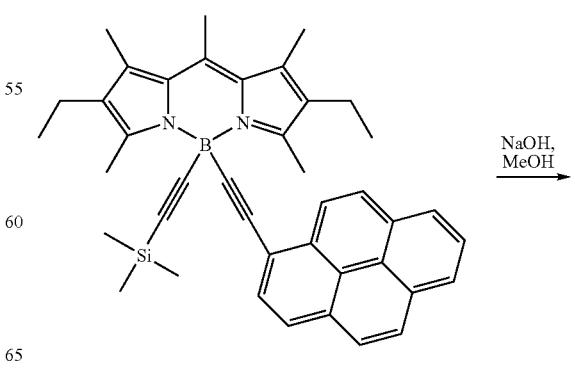

-continued

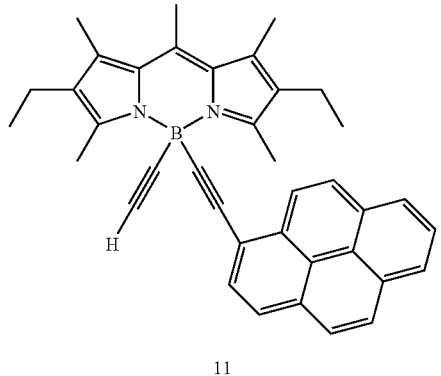

11

NaOH (28 mg, 5 eq) in 5 ml of MeOH was added to a solution of compound 10 (85 mg, 0.14 mmol) in 10 ml of CH$_2$Cl$_2$. The solution was stirred at ambient temperature for 4 days until the starting material had completely disappeared (monitored by TLC). Water was then added (10 ml) and the solution was extracted with dichloromethane (50 ml). After evaporation, the organic residue was purified by chromatography on a column of silica (CH$_2$Cl$_2$/cyclohexane, 30:70), and was then recrystallised in a CH$_2$C$_{1-2}$/hexane mixture in order to yield compound 11 (49 mg, 67%).

Characterisation of Compound 11

$^1$H NMR (CDCl$_3$ 400 MHz): δ=8.55 (d, IH, $^3$J=9.2 Hz), 8.17-8.13 (m, 2H), 8.07-7.95 (m, 6H), 2.93 (s, 6H), 2.68 (s, 3H), 2.50 (q, 4H, $^3$J=7.5 Hz), 2.40 (s, 6H), 2.67 (s, 1H), 1.12 (t, 6H, $^3$J=7.5 Hz), 0.18 (s, 9H);

$^{13}$C NMR (CDCl$_3$, 100 MHz): 152.0, 139.9, 134.8, 132.9, 132.1, 131.5, 131.3, 130.4, 130.3, 129.8, 127.8, 127.53, 127.46, 126.4, 126.1, 125.2, 124.6, 124.4, 120.5, 17.6, 17.5, 15.2, 14.8, 14.3;

$^{11}$B NMR (CDCl$_3$, 128 MHz): −10.1 (s);

UV-Vis (CH$_2$Cl$_2$) λnm (ϵ, M$^{-1}$ cm$^{-1}$) 516 (60700), 367 (42000), 349 (31500), 285 (46000), 274 (27600), 248 (42000), 241 (39500).

EXAMPLE 12

Preparation of Compound 12

Compound 12 was prepared according to the following reaction pattern.

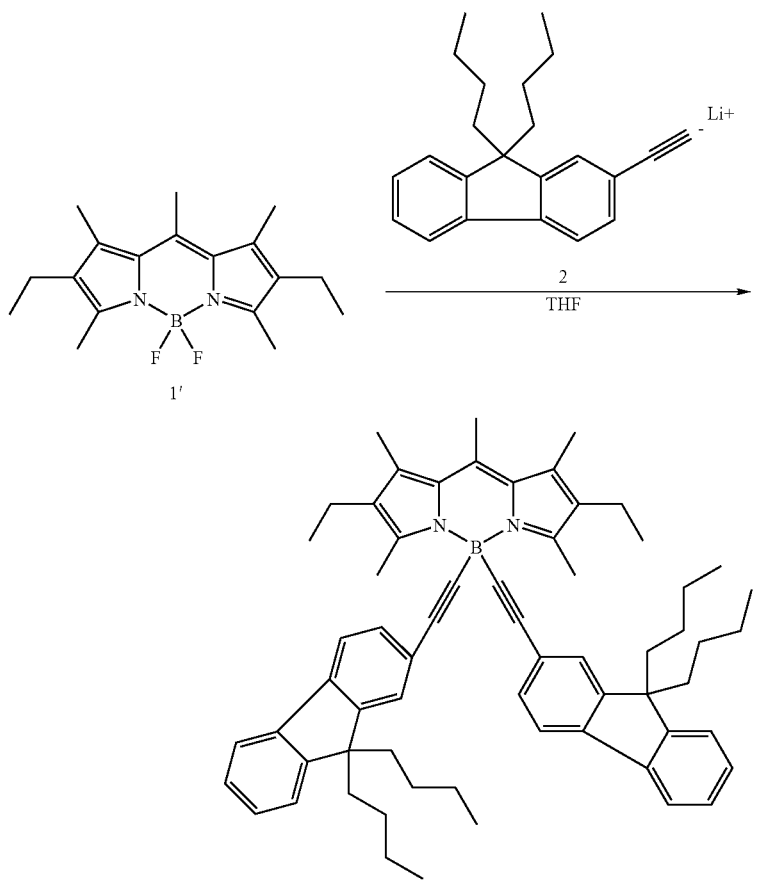

12 n-butyllithium (1.74 M, 0.18 ml) was added to a solution of 2-ethynylfluorene (95 mg, 0.31 mmol) in anhydrous THF (10 ml), under argon at −78° C. The mixture was stirred for one hour at −78° C., then at ambient temperature for 30 minutes. The solution was then transferred by cannula into a solution of 4,4-difluoro-1,3,5,7,8-pentamethyl-2,6-diethyl-4-bora-3a,4a-diaza-s-indacene 1' (50 mg, 0.16 mmol) in anhydrous THF (10 ml). The solution was stirred at ambient temperature for 30 minutes until the starting material had completely disappeared (monitored by TLC). Water was then added (5 ml) and the mixture was extracted using $CH_2Cl_2$ (20 ml). After evaporation, the organic material was purified by chromatography on a column of silica ($CH_2Cl_2$/cyclohexane, 20:80). After recrystallisation in a $CH_2Cl_2$/hexane mixture, compound 12 (50 mg, 38%) was obtained.

Characterisation of Compound 12

$^1$H NMR (CDCl$_3$ 400 MHz): δ=7.65-7.62 (m, 2H), 7.55. (d, 2H, $^3J$=7.7 Hz), 7.39-7.26 (m, 10H), 2.96 (s, 6H), 2.67 (s, 3H), 2.52 (q, 4H, $^3J$=7.5 Hz), 2.40 (s, 6H), 1.92 (t, 8H$f^3J$=8.3 Hz), 1.14 (t, 6H, $^3J$=7.5 Hz), 1.05 (q, 8H, $^3J$=7.2 Hz), 0.6 (t, 12H, $^3J$=7.2 Hz), 0.58-0.50 (m, 8H);

$^{13}$C NMR (CDCl$_3$, 100 MHz): 152.1, 151.0, 150.4, 141.0, 140.2, 139.8, 134.6, 132.7, 130.8, 130.3, 127.1, 126.8, 125.9, 124.1, 122.9, 119.8, 119.3, 55.0, 40.4, 26.0, 23.2, 17.7, 17.5, 15.2, 14.9, 14.3, 13.9;

$^{11}$B NMR (CDCl$_3$, 128 MHz): −9.6 (s);

UV-Vis (CH$_2$Cl$_2$) λnm (ϵ, M$^{-1}$ cm$^{-1}$)=517 (70000), 323 (80000), 297 (62100), 228 (38500).

EXAMPLE 13

Preparation of Compound 13

Compound 13 was prepared according to the following reaction pattern.

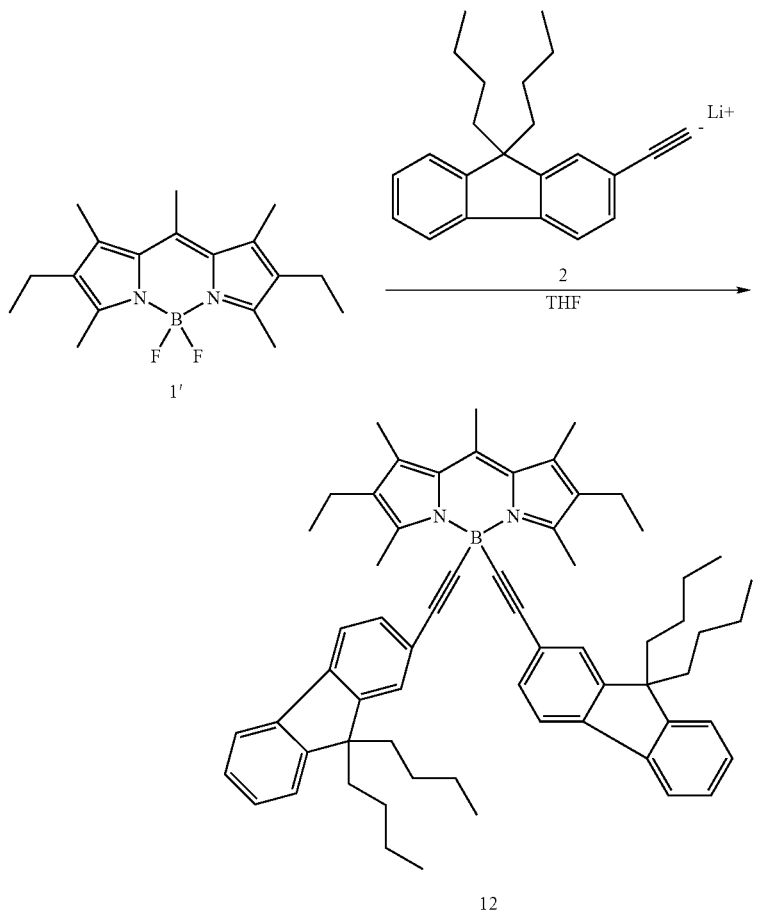

n-butyllithium (1.74 M, 93 μL) was added to a solution of 1-ethynylperylene (45 mg, 0.16 mmol) in anhydrous THF (5 ml) under argon at −78° C. The mixture was stirred for one hour at −78° C., then at ambient temperature for 30 minutes. The solution was then transferred by cannula into a solution of 4,4-difluoro-1,3,5,7,8-pentamethyl-2,6-diethyl-4-bora-3a,4a-diaza-s-indacene (100 mg, 0.082 mmol) in anhydrous THF (10 ml). The solution was stirred at ambient temperature for 30 minutes until the starting material had completely disappeared (monitored by TLC). Water was then added (5 ml) and the mixture was extracted using CH$_2$Cl$_2$ (20 ml). After evaporation, the organic material was purified by chromatography on a column of silica (CH$_2$Cl$_2$/cyclohexane, 20:80). After recrystallisation in a CH$_2$Cl$_2$/hexane mixture, the desired product was obtained (20 mg, 15%).

Characterisation of Compound 13

$^1$H NMR (CDCl$_3$ 400 MHz): δ=8.37. (d, 2H, $^3$J=8.1 Hz), 8.21-8.13 (m, 6H), 8.08. (d, 2H, $^3$J=8.1 Hz), 7.67-7.65 (m, 4H), 7.61 (d, 2H, $^3$J=7.9 Hz), 7.51-7.43 (m, 6H), 3.00 (s, 6H), 2.71 (s, 3H), 2.52 (q, 4H, $^3$J=7.5 Hz), 2.43 (s, 6H), 1.13 (t, 6H, $^3$J=7.5 Hz);

$^{13}$C NMR (CDCl$_3$, 100 MHz): 152.1, 135.4, 134.8, 134.7, 132.9, 131.5, 131.4, 131.3, 130.6, 130.5, 128.7, 127.9, 127.1, 127.0, 126.7, 123.0, 120.63, 120.57, 120.4, 119.9, 17.6, 17.5, 15.3, 14.9, 14.5;

$^{11}$B NMR (CDCl$_3$, 128 MHz): −9.4 (s);

UV-Vis (CH$_2$Cl$_2$) λnm (ϵ, M$^{-1}$ cm$^{-1}$)=517 (53500), 462 (93000), 435 (64500), 410 (30500), 259 (83000), 228 (83000).

Figure 9:
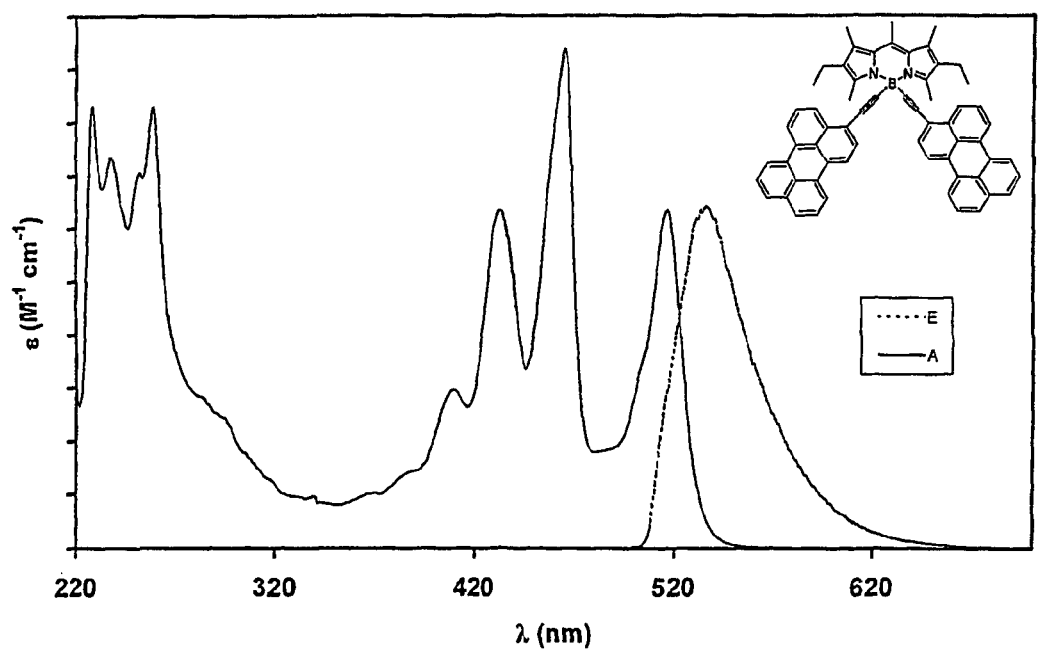
FIG. 9 shows the absorption spectrum (solid line, labelled A) and the emission spectrum (dotted line, labelled E) ($\lambda_{exc}$=526 nm) of compound 13.

FIG. 9 shows the absorption spectrum (solid line, labelled A) and the emission spectrum (dotted line, labelled E) (λ$_{exc}$=526 nm) of compound 13.

Figure 10:
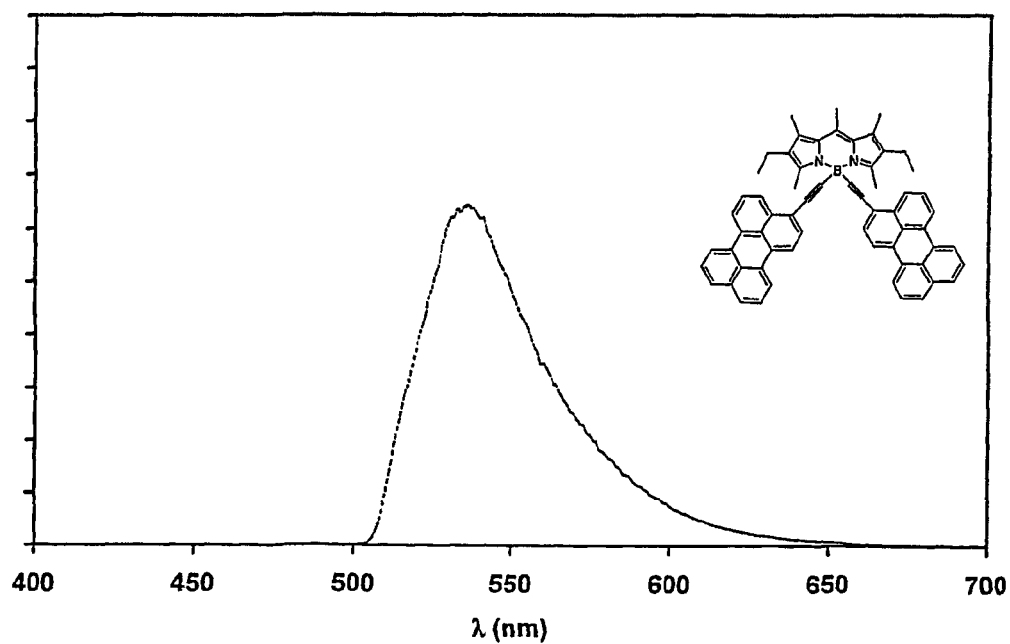
FIG. 10 shows the emission spectrum of compound 13 with $\lambda_{exc}$ at 369 nm, and a quantum yield of 94%.

FIG. 10 shows the emission spectrum of compound 13 with λ$_{exc}$ at 462 nm, and a quantum yield of 94%.

EXAMPLE 14

Preparation of Compound 14

Compound 14 was prepared according to the following reaction pattern.

Characterisation of Compound 14

$^1$H NMR (CDCl$_3$ 300 MHz): δ=7.89 (s, 2H), 7.77-7.68 (m, 6H), 2.93 (s, 6H), 2.67 (s, 3H), 2.50 (q, 4H, $^3$J=7.5 Hz), 2.39 (s, 6H), 1.12 (t, 6H, $^3$J=7.5 Hz);

$^{13}$C NMR (CDCl$_3$, 75 MHz): 152.1, 139.8, 134.6, 133.2, 132.7, 132.4, 130.9, 130.3, 129.2, 127.7, 127.6, 127.5, 126.2, 125.9, 123.1, 17.6, 17.4, 15.2, 14.8, 14.2;

$^{11}$B NMR (CDCl$_3$, 128 MHz); −9.63 (s);

UV-Vis (CH$_2$Cl$_2$) λnm (ϵ, M$^{-1}$ cm$^{-1}$)=517 (77700), 303 (29900), 292 (34500), 284 (27300), 255 (110000), 246 (97500);

IR (KBr): ν=3413 (s), 2961 (s), 2172 (s), 1554 (s), 1184 (s), 1184 (s), 978 (s);

FAB$^+$ m/z (nature of peak, relative intensity): 583.1 ([M+H]$^+$, 100), 431.2 ([M-naphtha-≡]$^+$, 15);

Elemental analysis calculated for C$_{42}$H$_{39}$BN$_2$: C, 86.59; H, 6.75; N, 4.81. Found: C, 86.32; H, 6.52; N, 4.62.

EXAMPLE 15

Preparation of Compound 15

Compound 15 was prepared according to the following reaction pattern.

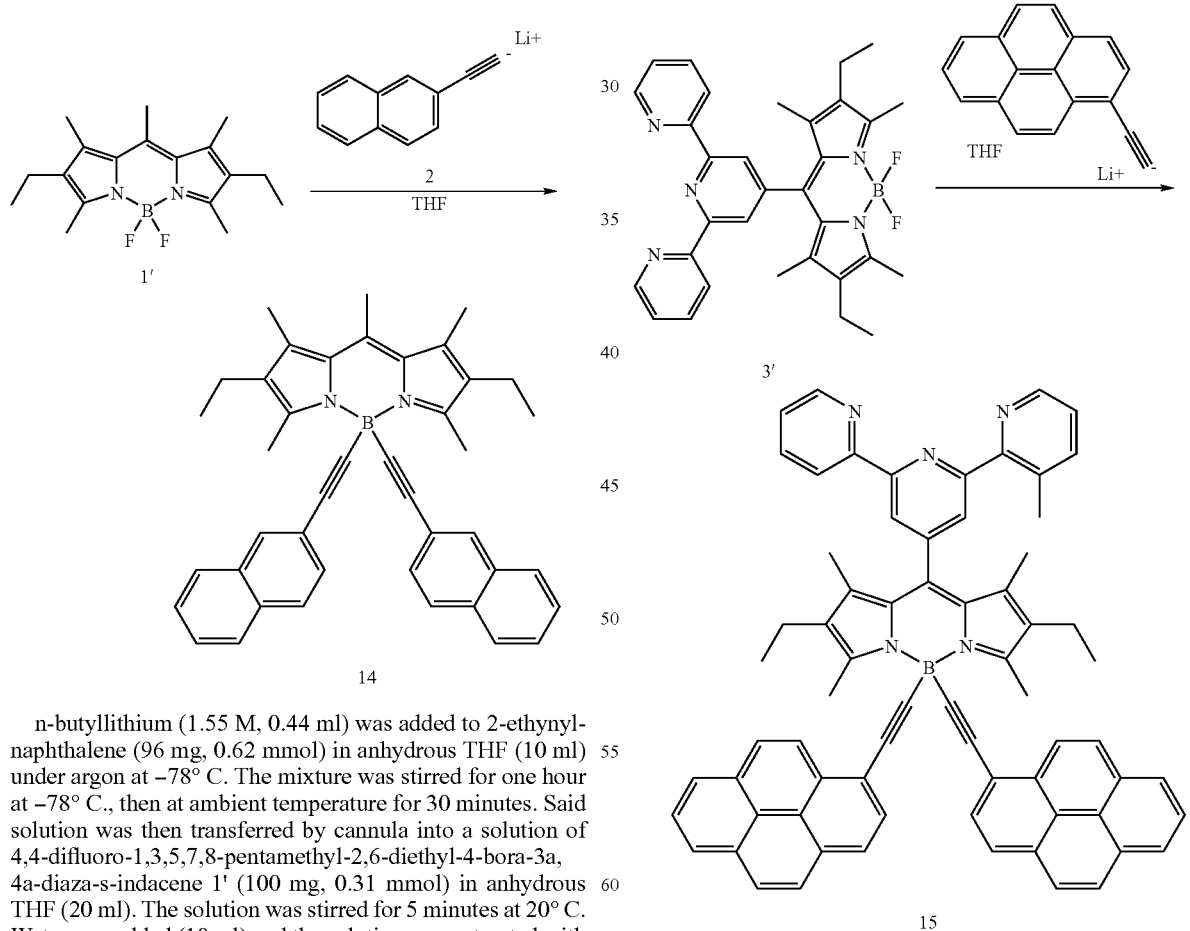

n-butyllithium (1.55 M, 0.44 ml) was added to 2-ethynyl-naphthalene (96 mg, 0.62 mmol) in anhydrous THF (10 ml) under argon at −78° C. The mixture was stirred for one hour at −78° C., then at ambient temperature for 30 minutes. Said solution was then transferred by cannula into a solution of 4,4-difluoro-1,3,5,7,8-pentamethyl-2,6-diethyl-4-bora-3a, 4a-diaza-s-indacene 1' (100 mg, 0.31 mmol) in anhydrous THF (20 ml). The solution was stirred for 5 minutes at 20° C. Water was added (10 ml) and the solution was extracted with CH$_2$Cl$_2$ (50 ml). After evaporation, the organic residue was purified by chromatography on a column of alumina (CH$_2$Cl$_2$/cyclohexane, 10:90), and was then recrystallised in a CH$_2$Cl$_2$/hexane mixture in order to yield pure compound 15 (130 mg, 72

The 4,4-difluoro-8-(2,2':6',2''-terpyridine-4'-yl)-1,3,5,7-tetramethyl-2,6-diethyl-4-bora-3a,4a-diaza-s-indacene was prepared according to the following mode of operation. 0.5 g (1.91 mmol) of 4'-(formyl-2,2':6,2''-terpyridine) and 0.57 ml (4.2 mmol) of 3-ethyl-2,4-dimethyl-pyrrole were stirred in trifluoroacetic acid for a week at ambient temperature, then 0.42 g (1.9 mmol) of dicyanodichloroquinone were added, and the mixture was stirred for four more hours. 0.5 ml of triethylamine and 0.35 ml of $BF_3.Et_2O$ were subsequently added and the solution was stirred for another day. Lastly, the mixture was washed with a saturated $NaHCO_3$ solution, the organic phase was dried and then subjected to chromatography over alumina (hexane/dichloromethane, 7:3) to yield 0.73 g of compound 3'.

n-butyllithium (1.55 M, 0.15 ml) was added to 1-ethynylpyrene (41 mg, 0.179 mmol) in anhydrous THF (5 ml) under argon at −78° C. The mixture was stirred for one hour at −78° C., then at ambient temperature for 30 minutes. The dark green solution was then transferred by cannula into a solution of 4,4-difluoro-8-(2,2':6',2"-terpyridine-4'-yl)-1,3,5,7-tetramethyl-2,6-diethyl-4-bora-3a,4a-diaza-s-indacene 3' (48 mg, 0.089 mmol) in anhydrous THF (10 ml). The solution was stirred at ambient temperature for 10 minutes until the starting material had completely disappeared (monitored by TLC). Water was then added (5 ml) and the solution was extracted with dichloromethane $CH_2Cl_2$ (20 ml). After evaporation, the organic fraction was purified by chromatography on a column of alumina ($CH_2Cl_2$/cyclohexane, 20:80), and was then recrystallised in $CH_2Cl_2$/hexane to yield the desired product 15 (25 mg, 30%).

Characterisation of Compound 15

$^1H$ NMR ($CDCl_3$ 400 MHz): δ=8.82 (d, 2H, $^3J$=9.0 Hz), 8.75-8.69 (m, 6H), 8.22-7.98 (m, 16H), 7.91 (dt, 2H, $^3J$=8.0 Hz, $^4J$=2.0 Hz), 7.37 (m, 2H), 3.15 (s, 6H), 2.45 (q, 4H, $^3J$=7.6 Hz), 1.57 (s, 6H), 1.09 (t, 6H, J=7.5 Hz);

$^{13}C$ NMR ($CDCl_3$, 75 MHz): 156.4, 155.7, 154.6, 149.5, 147.1, 137.0, 136.3, 133.6, 132.3, 131.5, 131.4, 130.5, 129.9, 128.6, 128.0, 127.6, 127.5, 126.5, 126.1, 125.3, 125.2, 124.75, 124.70, 124.6, 124.3, 121.5, 121.3, 120.8, 17.2, 15.0, 14.7, 12.9;

$^{11}B$ NMR ($CDCl_3$, 128 MHz); −8.92 (s);

UV-Vis ($CH_2Cl_2$) λnm (ε, $M^{-1}$ $cm^{-1}$=526 (70000), 370 (103000), 358 (78000), 285 (111400), 275 (74400), 248 (106000);

IR (KBr): ν=2961 (s), 2164 (m), 1582 (s), 1402 (s), 1178 (s), 978 (s), 845 (s);

$FAB^+$ m/z (nature of peak, relative intensity): 948.2 ([M+H]$^+$, 100), 722.2 ([M-pyr-≡]$^+$, 20);

Elemental analysis calculated for $C_{68}H_{50}BN_5$: C, 86.16; H, 5.32; N, 7.39. Found: C, 85.95; H, 5.12; N, 7.27.

EXAMPLE 16

This compound has an acid group which is protected in the form of oxazoline and which can be unprotected by methods known to the person skilled in the art.

Preparation of Compound 16

Compound 16 was prepared according to the following reaction pattern.

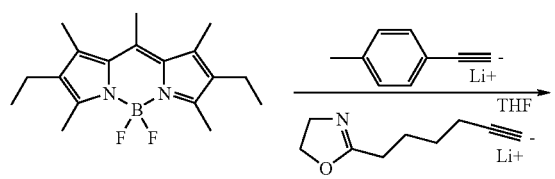

-continued

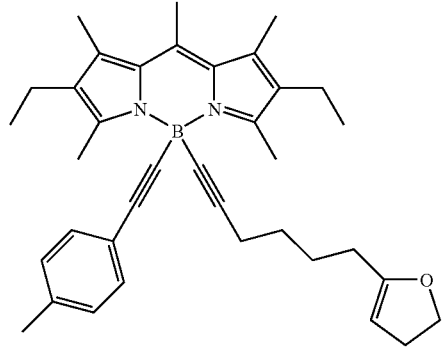

18

6-oxazoline-hex-1-yne (47 mg, 0.31 mmol) and p-ethynyltoluene (40 µL, 0.31 mmol) were dissolved in anhydrous THF (5 ml) under argon in two different Schlenk tubes. n-Butyllithium (1.34 M in n-hexane, 0.23 ml) was added to each Schlenk tube at −78° C. and the two solutions were stirred for one hour at −78° C., then at ambient temperature for 30 minutes. The two solutions were then simultaneously transferred by cannula into a solution of 4,4-difluoro-1,3,5,7,8-pentamethyl-2,4-diethyl-4-bora-3a,4a-diaza-s-indacene 1' (100 mg, 0.31 mmol) in anhydrous THF (20 ml) at ambient temperature. The solution was stirred at ambient temperature for 20 minutes until the starting material had completely disappeared (monitored by TLC). Water was then added (5 ml) and the solution was extracted with $CH_2Cl_2$ (20 ml). After evaporation, the organic material was purified by chromatography on a column of silica ($CH_2Cl_2$/cyclohexane, 20:80), then recrystallised in a $CH_2Cl_2$/hexane mixture in order to obtain pure compound 16 (22 mg, 13%).

Characterisation of Compound 16

$^1H$ NMR($C_6D_6$, 300 MHz): δ=7.43 (d, 2H, $^3J$ 8.1 Hz), 6.76 (s, 2H, $^3J$=8.1 Hz), 3.59 (t, 2H, $^3J$=8.8 Hz), 3.43 (t, 2H, $^3J$=8.8 Hz), 3.11 (s, 6H), 2.26 (q, 4H$^3J$=7.5 Hz), 2.17-2.11 (m, 4H), 2.01 (s, 3H), 1.99 (s, 6H), 1.95 (s, 3H), 1.80-1.70 (m, 2H), 1.50-1.42 (m, 2H), 0.94 (t, 6H, $^3J$=7.5 Hz);

$^{13}C\{^1H\}$ NMR($C_6D_6$, 75 MHz): 167.3, 151.9, 140.0, 136.6, 133.9, 132.4, 131.9, 130.8, 129.1, 66.7, 54.9, 30.5, 29.2, 27.8, 25.7, 21.2, 20.0, 17.7, 16.9, 15.2, 14.5;

$^{11}B$ $\{^1H\}$. NMR($C_6D_6$, 128 MHz): −9.40 (s);

UV-Vis ($CH_2Cl_2$) λnm (ε, $M^{-1}$ $cm^{-1}$)=515 (54700), 370 (4350), 262 (24000), 251 (24500).

EXAMPLE 17

This compound has an acid group which is protected in the form of oxazoline and which can be unprotected by methods known to the person skilled in the art.

Preparation of Compound 17

Compound 17 was prepared according to the following reaction pattern.

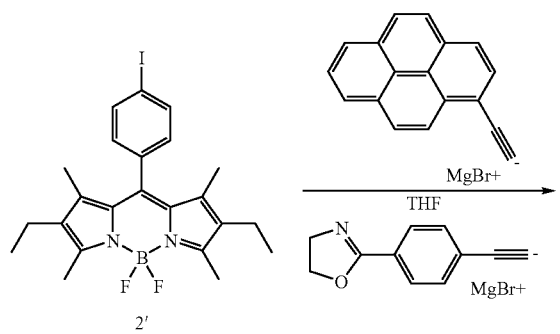

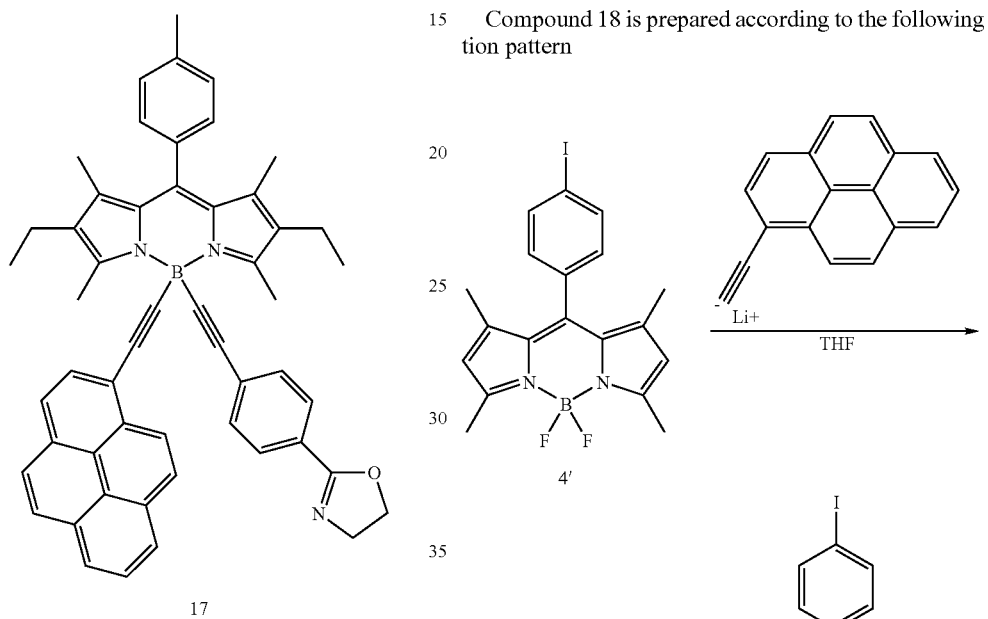

17

Phenyl-1-ethynyl-4-oxazoline (35 mg, 0.20 mmol) and 1-ethynylpyrene (45 mg, 0.2 mmol) were dissolved in anhydrous THF (5 ml) under argon in two different Schlenk tubes. Ethylmagnesium bromide (1.0 M in THF, 0.2 ml) was added to each Schlenk tube at −78° C. and the two solutions were stirred at ambient temperature for three hours. The two anionic solutions were simultaneously transferred by cannula into a solution of 4,4-difluoro-8-(4-iodophenyl)-1,3,5,7-tetramethyl-4-bora-3a,4a-diaza-s-indacene 2' (100 mg, 0.2 mmol) in anhydrous THF (20 ml). The solution was heated to reflux overnight until the difluorinated starting product had completely disappeared (monitored by TLC). Water (5 ml) was subsequently added and the solution was extracted with $CH_2Cl_2$ (20 ml). After evaporation, the organic material was purified by chromatography on a column of silica ($CH_2Cl_2$/cyclohexane, 20:80), then recrystallised in a $CH_2Cl_2$/hexane mixture in order to yield compound 17 (35 mg, 26%).

Characterisation of Compound 17

$^1$H NMR (CDCl$_3$, 200 MHz): δ=8.62 (d, 1H, $^3$J=9.1 Hz) 8.18-7.83 (m, 12H), 7.51 (d, 2H, $^3$J=8.6 Hz), 7.19-7.13 (m, 2H), 4.47 (t, 2H, $^3$J=9.1 Hz), 4.08 (t, 2H, $^3$J=9.1 Hz), 2.99 (s, 6H), 2.42 (q, 4H, $^3$J=7.5 Hz), 1.39 (s, 6H), 1.08 (t, 6H, $^3$J=7.5 Hz);

$^{13}$C NMR {$^1$H} (C$_6$D$_6$, 75 MHz): 167.6, 154.6, 138.3, 136.6, 136.3, 132.0, 130.8, 130.7, 130.1, 129.7, 129.1, 128.7, 126.6, 126.3, 125.6, 125.5, 125.2, 124.9, 67.2, 55.3, 17.6, 14.7, 14.9, 12.1;

$^{11}$B NMR {$^1$H} (C$_6$D$_6$, 128 MHz): −8.56 (s);

UV-Vis (CH$_2$Cl$_2$) λnm (ε, M$^{-1}$ cm$^{-1}$)=525 (58200) 380 (50700), 350 (38100), 286 (90500), 276 (78100), 249 (64300).

Figure 11:
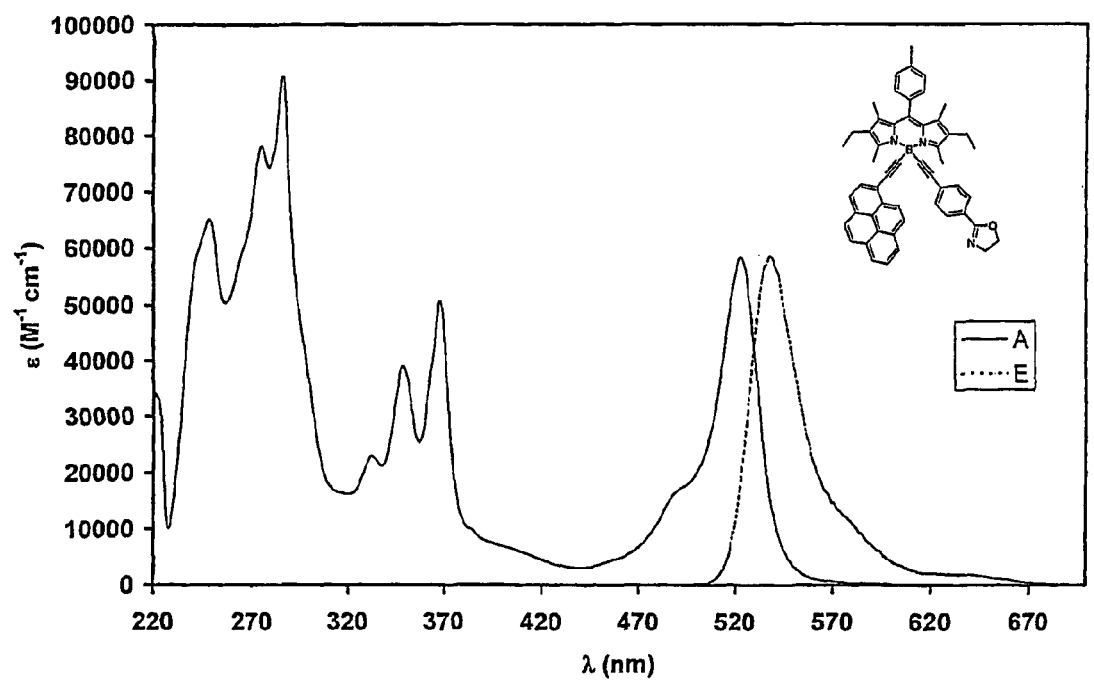
FIG. 11 shows the absorption spectrum (solid line, labelled A) and the emission spectrum (dotted line, labelled E) ($\lambda_{exc}$=516 nm) of compound 17.

FIG. 11 shows the absorption spectrum (solid line, labelled A) and the emission spectrum (dotted line, labelled E) ($λ_{exc}$=516 nm) of compound 17.

Figure 12:
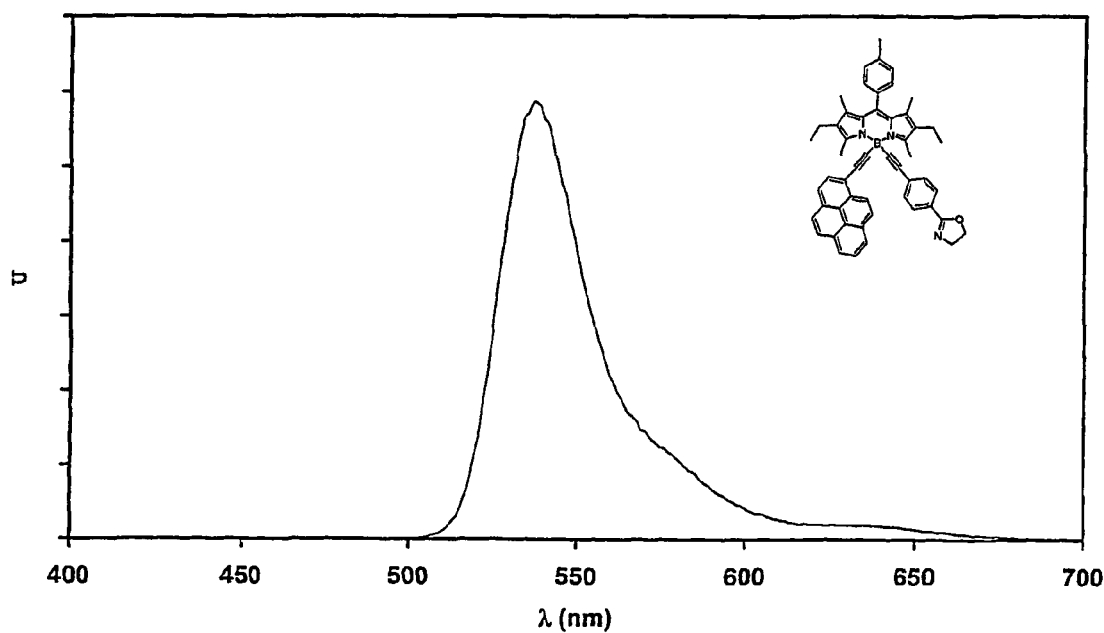
FIG. 12 shows the emission spectrum of compound 17 with $\lambda_{exc}$ at 380 nm, and a quantum yield of 53%.

FIG. 12 shows the emission spectrum of compound 17 with $λ_{exc}$ at 380 nm, and a quantum yield of 53%.

EXAMPLE 18

Preparation of Compound 18

Compound 18 is prepared according to the following reaction pattern

The 4,4-difluoro-1,3,5,7-tetramethyl-8-(p-iodophenyl)-4-bora-3a,4a-diaza-s-indacene 4' was prepared according to the following mode of operation. 1.17 g of p-iodo-benzoyle chloride and 1 ml of 2,4-dimethyl-pyrrole were stirred for one day at ambient temperature. 3.7 ml of triethylamine and 4.5 ml of BF$_3$Et$_2$O were subsequently added. The mixture was stirred overnight, and the organic phase was subsequently washed with water. Chromatography over alumina (hexane/dichloromethane, 7:3) and recrystallisation in a hexane/dichloromethane mixture yielded 0.9 g of compound 4'.

A solution of n-butyllithium 1.27 M in hexane (0.304 ml) was added to a solution of 1-ethynylpyrene (100 mg, 0.44 mmol) in anhydrous THF (10 ml) under argon at −78° C. The mixture was stirred for 1 hour at −78° C., then at ambient temperature for 30 minutes. The solution thus obtained was transferred by cannula into a solution of 4,4-difluoro-1,3,5,7-tetramethyl-8-(p-iodophenyl)-4-bora-3a,4a-diaza-s-indacene (80 mg, 0.176 mmol) in anhydrous THF (10 ml). The solution was stirred for 15 minutes at ambient temperature until the starting material had disappeared (monitored by TLC), then water was added (10 ml). Said solution was extracted with dichloromethane (20 ml). After evaporation, the organic residue was purified by chromatography on a column of alumina ($CH_2Cl_2$/cyclohexane, with a gradient of from 90:10 to 70:30), and was then recrystallised in a $CH_2Cl_2$/cyclohexane mixture in order to obtain compound 7 in the form of orange crystals (76 mg, 50%).

Characterisation of Compound 20

$^1$H NMR ($CDCl_3$ 400 MHz): δ=8.79 (d, 2H, $^3$J=9.3 Hz), 8.18-7.99 (m, 16H), 7.89 (d, 2H$^3$J=8.5 Hz), 7.21 (d, 2H, $^3$J=8.2 Hz), 6.20 (s, 2H), 3.17 (s, 6H), 1.53 (s, 6H)

$^{13}$C NMR ($CDCl_3$, 100 MHz): 156.3, 141.6, 140.7, 138.6, 135.6, 132.5, 131.7, 131.6, 130.9, 130.7, 130.1, 128.3, 127.9, 127.7, 126.6, 126.4, 125.5, 125.0, 124.9, 124.8, 122.4, 120.7, 95.4, 94.9, 17.0, 15.4;

$^{11}$B NMR ($CDCl_3$, 128 MHz); −8.87 (s);

UV-Vis ($CH_2Cl_2$) λnm (ϵ, $M^{-1}$ $cm^{-1}$)=501 (70000) 471sh (6200), 369 (89000), 349 (69700), 285 (94000)

EXAMPLE 19

Preparation of Compound 19

Compound 19 is prepared according to the following reaction pattern

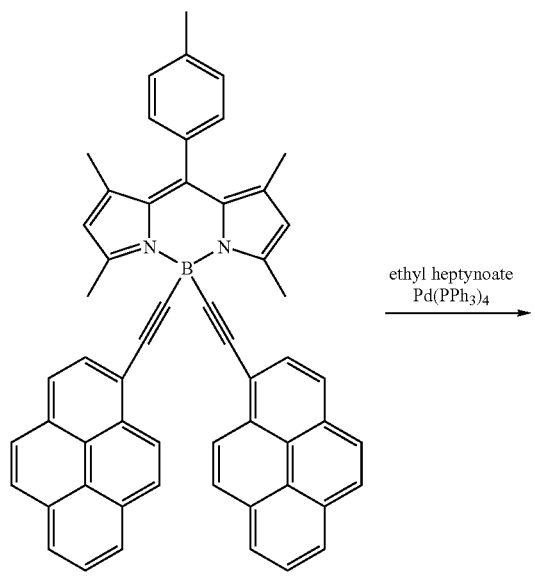

18

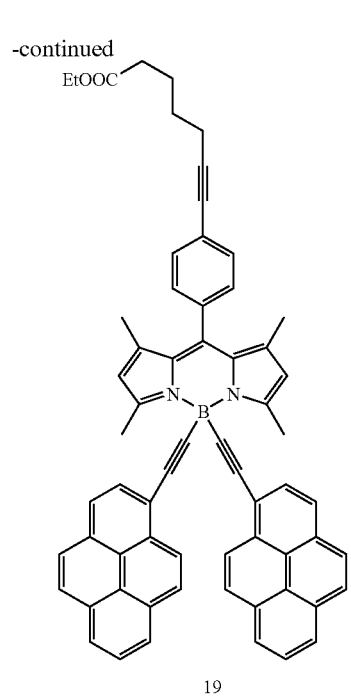

19

A solution of compound 18 (0.07 g, 0.081 mmol) and heptynoic ester (0.025 g, 0.162 mmol) was degassed for 30 minutes in a THF/iPr$_2$NH mixture (10/1.5 ml). Pd (II) $Cl_2$ $(PPh_3)_2$ (4 mg, 6 mole %) and CuI (2 mg, 10 mole %) were subsequently added and the mixture was stirred at ambient temperature for 16 hours. After the reaction had finished, 50 ml of water were added and the organic phases were extracted with $CH_2Cl_2$ (30 ml) and then dried with $MgSO_4$. Ester was obtained after purification on a chromatography column over alumina (eluant: cyclohexane/$CH_2Cl_2$ 80/30) followed by recrystallisation in $CH_2Cl_2$/hexane (amount obtained: 0.06 g, 83%).

Characterisation of Compound 19

$^1$H NMR ($CDCl_3$ 300 MHz): δ=8.80 (d, 2H, $^3$J=9.2 Hz), 8.18-7.96 (m, 16H), 7.48 (ABsys, 4H, $J_{AB}$=8.3, voδ=58.5 Hz), 6.20 (s, 2H), 4.16 (q, 2H, $^3$J=6 Hz), 3.17 (s, 6H), 2.49-2.37 (m, 4H), 1.90-1.69 (m, 4H), 1.53 (s, 6H), 1.28 (t, 3H, $^3$J=6 Hz).

$^{13}$C NMR ($CDCl_3$, 100 MHz): 173.4, 1555.7, 141.4, 141.3, 134.9, 132.2 (CH), 132.1, 131.3, 131.2, 130.4, 129.8, 129.7 (CH), 128.4 (CH), 127.9 (CH), 127.5 (CH), 127.3 (CH), 126.2 (CH), 126.0 (CH), 125.2 (CH), 125.1 (CH), 124.6, 124.5, 124.4 (CH), 121.9 (CH), 120.4, 94.9, 91.0, 82.6, 80.5, 60.3 ($CH_2$), 33.9 ($CH_2$), 30.9 ($CH_3$), 28.1 ($CH_2$), 24.3 ($CH_2$), 19.2 ($CH_2$), 16.6 ($CH_3$), 14.9 ($CH_3$)

UV-Vis ($CH_2Cl_2$) λnm (ϵ, $M^{-1}$ $cm^{-1}$)=501 (65900), 471sh (15900), 369 (87000), 349 (69500), 285 (94000).

Figure 13:
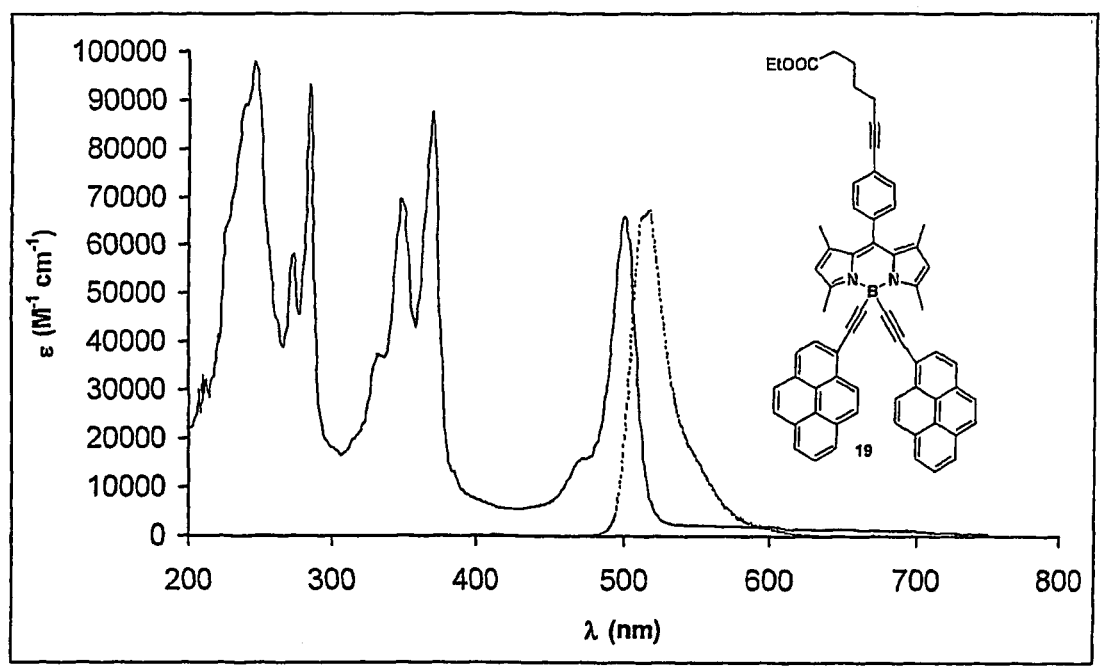
FIG. 13 shows the absorption spectrum (solid line, labelled A) and the emission spectrum (dotted line, labelled E) ($\lambda_{exc}$=501 nm) of compound 19.

FIG. 13 shows the absorption spectrum (solid line, labelled A) and the emission spectrum (dotted line, labelled E) ($λ_{exc}$=501 nm) of compound 19.

Figure 14:
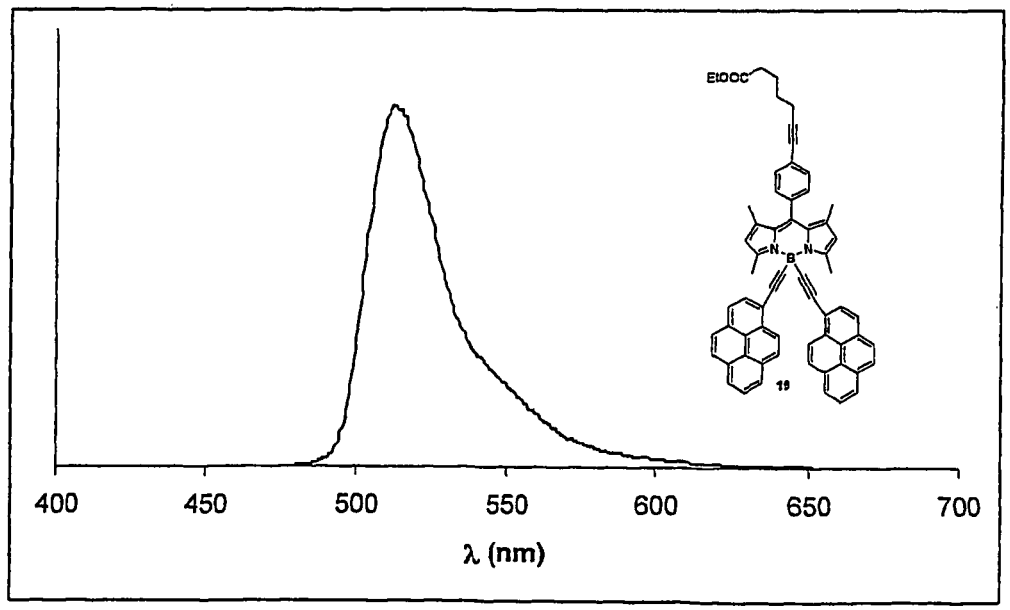
FIG. 14 shows the emission spectrum of compound 19 with $\lambda_{exc}$ at 369 nm, and a quantum yield of 40%.

FIG. 14 shows the emission spectrum of compound 19 with $λ_{exc}$ at 369 nm, and a quantum yield of 40%.

EXAMPLE 20

Preparation of Compound 20

Compound 20 is prepared according to the following reaction pattern from compound 3 and an aryl halide. This reaction is an example of a Sonogashira coupling on compound 3 intended to modify the substituents S1 and S2.

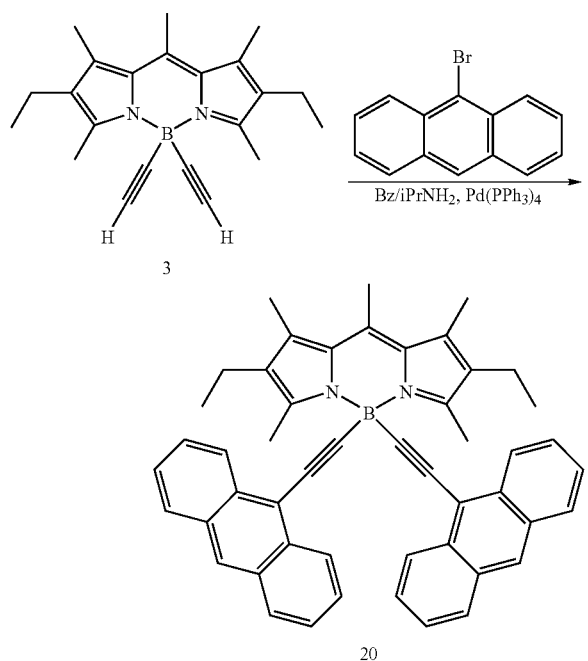

A benzene/iPr₂NH solution (50:50) containing 57 mg (0.18 mmol) of compound 3 and 92 mg (0.36 mmol) of 9-bromoanthracene was degassed for 20 minutes in a Schlenk vessel. 12.5 mg (6 mole %) of [Pd(PPh₃)₄] were subsequently added and the mixture was stirred and heated to 60° C. for 16 hours under argon. After the solvent had evaporated, subjecting the residue to chromatography over a support ($CH_2Cl_2$/cyclohexane, 10:90), followed by recrystallisation in $CH_2Cl_2$/hexane produced pure compound 20 (31 mg, 25%)

Characterisation of Compound 20

$^1$H NMR (CDCl₃ 400 MHz): δ=8.60-8.56 (m, 4H), 8.24 (s, 2H), 7.90-7.85 (m, 6H), 7.38-7.32 (m, 6H), 2.70 (s, 3H), 2.42 (q, 4H, $^3J$=7.5 Hz), 2.43 6H), 1.04 (t, 6H, $^3J$=7.5 Hz);

$^{13}$C {$^1$H} NMR (CDCl₃, 100 MHz): 132.9, 131.4, 128.5, 127.7, 126.1, 126.0, 125.7, 125.5, 123.0, 120.63, 120.57, 120.4, 119.9, 17.6, 17.5, 15.3, 14.93, 14.92;

$^{11}$B {$^1$H} NMR (CDCl₃, 128 MHz): −9.4 (s);

UV-Vis ($CH_2Cl_2$) λnm (s, M$^{-1}$ cm$^{-1}$)=517 (81300), 411 (40000), 390 (38000), 262 (173000); IR (KBr): ν=2960 (m), 2926 (m), 2146 (m), 1594 (m), 1554 (s), 1439 (s), 1185 (s), 1122 (m), 977 (m), 878 (m), 736 (m);

FAB⁺ m/z (nature of peak, relative intensity): 683.2 ([M+H]⁺, 100);

Analysis calculated for $C_{50}H_{43}BN_2$: C, 87.96; H, 6.35; N, 4.10. Found: C, 87.63; H, 5.97; N, 3.81.

The fluorescent properties of compounds 1 to 20 were determined. The table below shows the absorption wavelength $\lambda_{abs}$, the emission wavelength $\lambda_{em}$, the Stokes shift ΔS according to the formula $\Delta S=(1/\lambda_{abs})-(1/\lambda_{em})$, the molar absorption coefficient ε, and the relative quantum yield Φ measured in dichloromethane at 20° C. The relative quantum yield Φ was measured by using Rhodamine 6G in water (Φ=76%, $\lambda_{exc}$=488 nm) as reference, the exact measurement of the quantum yield of which by calorimetry is described in J. Phys. Chem., 83, 1979, 2581. With the exception of compounds 1, 2, 3, and 16 which do not have chromophoric groups in the ultraviolet/blue regions, all the compounds described in the Examples have a Stokes shift of between 3,000 and 12,300 cm$^{-1}$ when they are excited between 320 and 460 nm, and have very high quantum yields of fluorescence.

The ΔS of compounds 1', 2' and 3' is provided by way of comparison.

Compound 1' designates the compound 4,4-difluoro-1,3,5,7,8-pentamethyl-2,6-diethyl-4-bora-3a,4a-diaza-s-indacene which is to be compared with the compounds obtained in Examples 1, 4 and 10-13.

Compound 2' designates the compound 4,4-difluoro-1,3,5,7-tetramethyl-8-(p-iodophenyl)-2,6-diethyl-4-bora-3a,4a-diaza-s-indacene which is to be compared with the compounds obtained in Examples 7, 8 and 17.

Compound 3' designates the compound 4,4-difluoro-1,3,5,7-tetramethyl-8-(2,2':6',2''-terpyridin-4'-yl))-2,6-diethyl-4-bora-3a,4a-diaza-s-indacene which is to be compared with the compound obtained in Example 14.

Compound 4' designates the compound 4,4-difluoro-1,3,5,7-tetramethyl-8-(p-iodophenyl)-4-bora-3a,4a-diaza-s-indacene which is to be compared with the compounds obtained in Examples 18 and 19.

TABLE 2

| No. | $\lambda_{abs}$ (nm) | $\lambda_{em}$ (nm) | ΔS (cm$^{-1}$) | ε(M$^{-1}$cm$^{-1}$) | Φ |
|---|---|---|---|---|---|
| 1 | 515 | 535 | 725- | 68000 | 98% |
| 2 | 513 | 532 | 696 | 43000 | 95% |
| 3 | 514 | 534 | 728 | 80000 | 92% |
| 4 | 516 | 535 | 688 | 73000 | 94% |
|  | 371 | 535 | 8263 | 95000 | 90% |
|  | 350 | 535 | 9880 | 69000 | 92% |
| 5 | 523 | 538 | 533 | 73000 | 98% |
|  | 370 | 538 | 8440 | 140000 | 97% |
|  | 350 | 538 | 9984 | 100000 | 98% |
| 6 | 522 | 538 | 570 | 70300 | 80% |
|  | 371 | 538 | 8637 | 95000 | 78% |
|  | 352 | 538 | 9822 | 72500 | 78% |
| 7 | 522 | 537 | 535 | 60000 | 80% |
|  | 373 | 537 | 8188 | 75000 | 80% |
|  | 353 | 537 | 9707 | 66500 | 79% |
| 8 | 522 | 538 | 570 | 55000 | 98% |
|  | 372 | 538 | 8294 | 70000 | 95% |
|  | 353 | 538 | 9741 | 55000 | 95% |
| 9 | 522 | 538 | 570 | 61000 | 82% |
|  | 373 | 538 | 8222 | 88000 | 51% |
|  | 352 | 538 | 9822 | 70200 | 55% |
| 10 | 515 | 533 | 655 | 44200 | 90% |
|  | 368 | 533 | 8412 | 30300 | 92% |
|  | 342 | 533 | 10478 | 23000 | 95% |
| 11 | 516 | 532 | 588 | 60700 | 80% |
|  | 367 | 532 | 8451 | 42000 | 73% |
|  | 349 | 532 | 9856 | 31500 | 75% |
| 12 | 517 | 535 | 650 | 70000 | 95% |
|  | 323 | 535 | 12268 | 80000 | 90% |
|  | 297 | 535 | — | 62100 | 90% |
| 13 | 517 | 536 | 685 | 53000 | 94% |
|  | 462 | 536 | 2988 | 93000 | 93% |
|  | 435 | 536 | 4332 | 64500 | 90% |
| 14 | 517 | 535 | 650 | 78000 | 90% |
|  | 303 | 535 | 14300 | 30000 | 31% |
|  | 292 | 535 | 15554 | 34500 | 32% |
| 15 | 526 | 590 | 2062 | 70000 | 40% |
|  | 370 | 590 | 10078 | 103000 | 50% |
|  | 358 | 590 | 10984 | 78000 | 50% |
| 16 | 515 | 534 | 690 | 54700 | 73% |
| 17 | 525 | 539 | 495 | 58200 | 83% |
|  | 380 | 539 | 7763 | 50700 | 53% |
|  | 350 | 539 | 10078 | 38100 | 53% |
| 18 | 501 | 514 | 504 | 70000 | 40% |
|  | 369 | 514 | 7654 | 89000 | 37% |
|  | 349 | 514 | 9200 | 70000 | 41% |

TABLE 2-continued

| No. | $\lambda_{abs}$ (nm) | $\lambda_{em}$ (nm) | $\Delta S$ (cm$^{-1}$) | $\epsilon$(M$^{-1}$cm$^{-1}$) | $\Phi$ |
|---|---|---|---|---|---|
| 19 | 501 | 514 | 504 | 66000 | 47% |
|  | 370 | 514 | 7570 | 87000 | 40% |
|  | 350 | 514 | 9120 | 69500 | 42% |
| 20 | 517 | 538 | 755 | 81300 | 98% |
|  | 411 | 538 | 5750 | 41000 | 98% |
| 1' | 517 | 538 | 755 | 64500 | 83% |
| 2' | 524 | 537 | 460 | 75900 | 78% |
| 3' | 529 | 548 | 655 | 72000 | 87% |
| 4' | 500 | 510 | 392 | 47100 | 64% |

Comparing the properties of the compounds 1', 2', 3' and 4' with the compounds according to the present invention shows that replacing an atom F with a —C≡C-L'-A substituent generally increases the ΔS by at least 10 times. In addition, comparing compounds 6 and 18 shows two different emissions for each of the compounds under single excitation at around 370 nm. This property makes the molecules according to the invention very suitable for use in multicoloured labelling.

The invention claimed is:

1. A compound corresponding to formula (I)

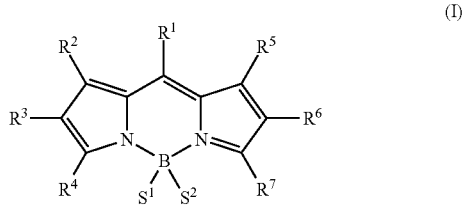

(I)

wherein:
each of the substituents R$^1$, R$^2$, R$^3$, R$^4$, R$^5$, R$^6$ and R$^7$ is selected independently of the other substituents from the group consisting of H, -L-H, -G and -L-G, or the two substituents R$^3$ and R$^4$ together form a divalent substituent Z$^{34}$ and/or the two substituents R$^6$ and R$^7$ together form a divalent substituent Z$^{67}$, said divalent substituents being such that they form, with the carbon atoms to which they are bound, a structure selected from the group consisting of one ring or two condensed rings, each ring having 5 or 6 atoms and comprising carbon atoms and at most two heteroatoms selected from N, O and S;

L is a binding group consisting of a single bond, or consisting of one or more segments selected from the alkylene groups and the linear or branched alkenylene groups optionally comprising in their chain one or more oxygen atoms forming ether substituents, alkynylenes and arylenes comprising a single ring or a plurality of condensed or non-condensed rings;

G is a functional group;

the substituents S$^1$ and S$^2$ each independently represent F; a substituent selected from the group defined for the substituents R$^1$ to R$^7$; or a group corresponding to formula —C≡C-L'-A, in which L' is a single bond or a substituent selected from the group defined for L, and A is a chromophoric group or a functional group capable of binding with a biological molecule, an inorganic compound, or a polymeric or non-polymeric organic compound; it being understood that at least one of S$^1$ and S$^2$ is a —C≡C-L'-A group.

2. The compound according to claim 1, wherein the binding group L consists of at least one segment selected from a single bond, an alkylene segment having from 1 to 10 carbon atoms, a phenylene segment, and of an alkynylene segment having from 2 to 4 carbon atoms, an alkenylene segment having from 2 to 4 carbon atoms and a polyether segment having from 1 to 12 oxygen atoms.

3. The compound according to claim 1, wherein group G is a polar group.

4. The compound according to claim 3, wherein the polar group is selected from the amide, sulphonate, sulphate, phosphate, quaternary ammonium, hydroxyl or phosphonate groups and polyethylene oxide segments.

5. The compound according to claim 1, wherein group G is an electron donor group or an electroattractive group.

6. The compound according to claim 3, wherein group G is selected from the cyano, nitro, fluoroalkyl, perfluoroalkyl, amide, nitrophenyl, substituted triazino, sulphonamide, alkenyl and alkynyl groups, and the binding group L is selected from alkenylene or alkynylene segments having from 2 to 4 carbon atoms.

7. The compound according to claim 1, wherein group G is a reactive functional group which allows said compound to be grafted onto a biological molecule.

8. The compound according to claim 1, wherein group G is a functional group capable of reacting with an organic compound or an inorganic compound, forming a strong bond (covalent or ionic bond) or a weak bond (hydrogen bond) with said compound.

9. The compound according to claim 1, wherein at least one of the substituents S$^1$ and S$^2$ is the —C≡C-L'-A group in which A is a chromophoric group.

10. The compound according to claim 1, wherein each of the substituents S$^1$ and S$^2$ is the —C≡C-L'-A group, in which A is a chromophoric group.

11. The compound according to claim 9, wherein L' is a single bond or an alkylene segment having from 1 to 10 carbon atoms or a polyether segment having from 1 to 12 carbon atoms and A represents a chromophoric group selected from:
aryl groups having an aromatic ring optionally carrying substituents;
aryl groups having at least two condensed rings and optionally carrying at least one substituent;
groups with dye properties.

12. The compound according to claim 11, wherein the aryl group having an aromatic ring optionally carrying substituents is selected from p-toluoyl, styrenyl, pyridinyl, oligopyridinyls, thienyl and pyrrolyl.

13. The compound according to claim 11, wherein the aryl group having at least two condensed rings is selected from naphthyl, pyrenyl, anthracenyl, phenanthrenyl, quinolyl, phenanthronyl, perylenyl, fluorenyl, carbazolyl and acridinyl, said groups optionally carrying at least one substituent.

14. The compound according to claim 11, wherein the group with dye properties is selected from coumarinyl, hydroxycoumarinyl, alkoxycoumarinyl, trisulphonatopyrenyl, cyanine, styrylpyridinium, naphthalimidinyl and phenylphenanthridium groups.

15. The compound according to claim 1, wherein at least one of the substituents S$^1$ and S$^2$ is the —C≡C-L'-A group or at least one of the substituents R$^1$ to R$^7$ is an -L-G group, in which A or G is a group which allows said compound to bind with another compound.

16. The compound according to claim 15, wherein L' or L is a single bond or an alkylene having from 1 to 10 carbon atoms or a polyether segment having from 1 to 12 carbon atoms.

17. The compound according to claim 15 which can be bound to a polymer, wherein group A or group G is selected from H, trialkylsilyl groups or a crosslinking group.

18. The compound according to claim 17, wherein the crosslinking group is selected from methacrylate, vinyl, styryl, anilino, pyrrolyl, thiophenyl, furyl, isocyanato, and epoxide groups.

19. The compound according to claim 15 which can be bound to a biological molecule, wherein group A or group G is selected from the group consisting of succinimidyl ester, sulphosuccinimidyl ester, isothiocyanate, isocyanate, iodoacetamide, maleimide, halosulphonyls, phosphoramidites, alkylimidates, arylimidates, halogenoacids, substituted hydrazines, substituted hydroxylamines, and carbodiimides.

20. The compound according to claim 15 which can be bound to an organic compound, wherein the functional group A or G is a functional group capable of forming strong bond (covalent or ionic bond) or a weak bond (hydrogen bond) with a compound to be detected.

21. The compound according to claim 20, wherein functional group A or G is selected from the amino, ureido, hydroxyl, sulphhydryl, carboxyl, carbonyl or crown ether groups.

22. The compound according to claim 15 which can be bound to an inorganic compound, wherein group A or group G is selected from the functional groups capable of forming strong bonds with inorganic materials.

23. The compound according to claim 22 which can be bound to titanium oxides, zeolites or alumina, wherein group A or G is a carboxylate group.

24. The compound according to claim 22 which can be bound to a metal, wherein group A or G is a thiol group or a thioether group.

25. The compound according to claim 22 which can be bound to silica and to the oxidised surface of silicon, wherein group A or G is a siloxane group.

26. The compound according to claim 1, wherein one of the substituents $S^1$ and $S^2$ is the —C≡C-L'-A group, and the other substituent is selected from F, mononuclear aryl groups optionally carrying a substituent and aryl groups comprising at least two condensed rings.

27. The compound according to claim 1, wherein the compound is symmetrical and corresponds to formula (II)

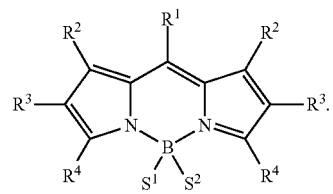

28. The compound according to claim 1, wherein the substituents $R^3$ and $R^4$ together form a cycle with the pentacycle carrying them, and the substituents $R^5$ and $R^7$ together form a cycle with the pentacycle carrying them.

29. The compound according to claim 28, wherein said compound corresponds to formula (III)

(III)

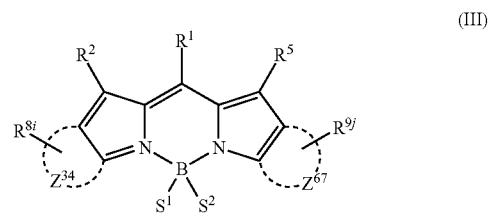

in which the substituents $R^{8i}$ and $R^{9j}$ are selected independently of one another from the group defined for the substituents $R^1$ to $R^7$.

* * * * *